United States Patent [19]

Antoine et al.

[11] Patent Number: 5,004,745
[45] Date of Patent: Apr. 2, 1991

[54] BENZO[1,8]NAPHTHYRIDINE DERIVATIVES, THEIR PREPARATION AND THE COMPOSITIONS WHICH CONTAIN THEM

[75] Inventors: Michel Antoine, Paris; Michel Barreau, Montgeron; Jean-Francois Desconclois, Paris; Philippe Girard, Arpajon; Guy Picaut, Chevilly Larue, all of France

[73] Assignee: Laboratoire Roger Bellon, Seine, France

[21] Appl. No.: 465,483

[22] Filed: Jan. 16, 1990

[30] Foreign Application Priority Data

Jan. 16, 1989 [FR] France ................... 89 00430
Jul. 28, 1989 [FR] France ................... 89 10218

[51] Int. Cl.$^5$ ............... A61K 31/495; A61K 31/395; C07D 401/14
[52] U.S. Cl. .................... 514/254; 514/218; 544/361; 540/575
[58] Field of Search ............ 544/361; 540/575; 514/218, 254

[56] References Cited

U.S. PATENT DOCUMENTS 4,133,885  1/1979  Bolhofer et al. ............. 546/122
4,229,456  10/1980 Bolhofer et al. ............. 546/122
4,594,347  6/1986  Ishikawa et al. ............. 544/361
4,705,789  11/1987 Grohe et al. ................ 544/361
4,720,495  1/1988  Takagi et al. ............... 544/361

Primary Examiner—Cecilia Shen
Attorney, Agent, or Firm—Morgan & Finnegan

[57] ABSTRACT

New benzo[b][1,8]naphthyridine derivatives of general formula (I) in which $R_1$ is a hydrogen atom or an alkyl or hydroxyalkyl radical, $R_2$ is a hydrogen atom or an alkyl, fluoroalkyl, cycloalkyl (3 to 6 C), alkoxy or alkylamino radical and $R_3$ is alkyl, $R_4$ and $R_5$ are different and are hydrogen or alkyl, or $R_3$ is H, alkyl or cycloalkyl and $R_4$ and $R_5$ are hydrogen, $R_6$ is hydrogen or fluorine and n is equal to 1 or 2, their salts, their preparation and the compositions which contain them.

These new products are used as antimicrobial agents

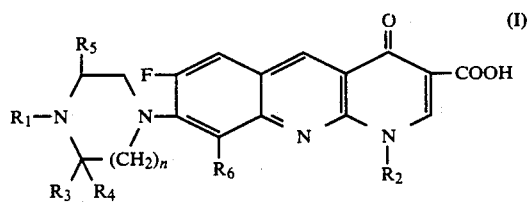

8 Claims, No Drawings

BENZO[1,8]NAPHTHYRIDINE DERIVATIVES, THEIR PREPARATION AND THE COMPOSITIONS WHICH CONTAIN THEM

DETAILED DESCRIPTION OF THE INVENTION

The present invention relates to new benzo[b][1,8-]naphthyridine derivatives of general formula:

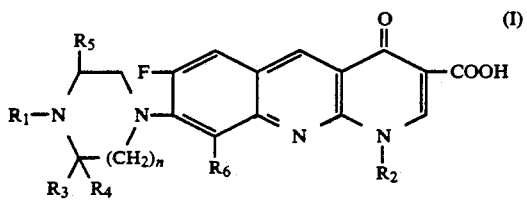

their salts, their preparation and the compositions which contain them.

Naphthyridine derivatives of structure:

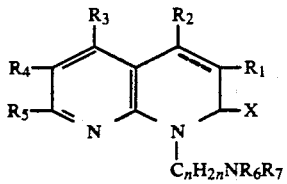

in which X can be oxygen and two adjacent radicals of the radicals $R_1$ to $R_5$ can form a benzene ring, have been described in U.S. Pat. Nos. 4,229,456 and 4,133,885.

These products are used as gastric acid secretion inhibitors.

German Patent Application No. 3,302,126 describes hypotensive agents of general formula:

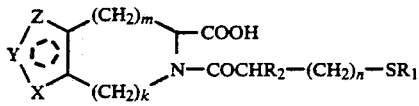

in which the radicals X, Y and Z can be O or a $NR_4$ radical or $CR_5=CR_5$ radical in which the $R_5$ can form a benzene ring.

It has been found that the products of general formula (I) in which:

$R_1$ represents a hydrogen atom or an alkyl or hydroxyalkyl radical, $R_2$ represents a hydrogen atom or an alkyl, fluoroalkyl, cycloalkyl, alkoxy or alkylamino radical, $R_3$ represents an alkyl radical, and $R_4$ and $R_5$ are different and represent a hydrogen atom or an alkyl radical, or $R_3$ represents a hydrogen atom or an alkyl or cycloalkyl radical and $R_4$ and $R_5$ are hydrogen atoms, $R_6$ represents a hydrogen or fluorine atom and n is equal to 1 or 2, and in which the alkyl radicals are straight-chain or branched and contain 1 to 4 carbon atoms and the cycloalkyl radicals contain 3 to 6 carbon atoms, as well as their salts and, where appropriate, their isomers, display a particularly valuable antibacterial activity.

The products of general formula (I) can exist in the hydrated form and it is understood that these hydrates also fall within the scope of the present invention.

According to the invention the products of general formula (I) can be obtained by substitution of a piperazine of general formula:

in which $R_1$, $R_3$, $R_4$, $R_5$ and n are as defined above, on a benzo[b][1,8]naphthyridine of general formula:

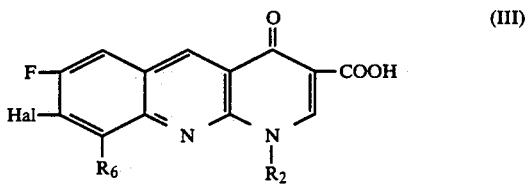

in which $R_2$ is defined as above and Hal is a fluorine, chlorine or bromine atom if $R_6$ is hydrogen, or Hal and are simultaneously fluorine atoms, followed, if appropriate, if $R_1$ is a hydrogen atom and if it is desired to obtain a benzo[b][1,8]naphthyridine derivative in which $R_1$ is methyl, by the conversion of the product obtained to a 8-(4-methyl-1-piperazinyl)benzo[b][1,8]naphthyridine.

The action of the piperazine derivative of general formula (II) generally takes place in the presence of an excess of this derivative as an acid acceptor or in the presence of an organic or inorganic acid acceptor in suitable organic solvents. It is possible to carry out the reaction with or without solvents, at a temperature between 30° and 120° C. When it is carried out in the presence of a solvent, the reaction advantageously takes place in solvents such as pyridine, dimethylformamide, dimethyl sulphoxide or acetonitrile.

It is understood that, in the case where the symbol $R_2$ in the product of general formula (III) is a hydrogen atom, it is preferable to protect this product beforehand. The protection and the removal of the protective radical after the reaction take place according to customary methods.

The protection can be effected by any group which is compatible and the use and removal of which do not alter the remainder of the molecule. In particular, the methods described by T. W. GREENE, Protective Groups in Organic Synthesis, A. Wiley-Interscience Publication (1981), or by McOMIE, Protective Groups in Organic Chemistry, Plenum Press (1973) are used.

By way of example, the protective groups can be chosen from the trimethylsilyl, methoxymethyl, ethoxymethyl, benzhydryl, trityl, tetrahyropyrannyl, formyl, acetyl, chloroacetyl, trichloroacetyl, trifluoroacetyl, methoxycarbonyl, ethoxycarbonyl, t-butoxycarbonyl and trichloroethoxycarbonyl radicals.

Where appropriate, the subsequent operation for methylation of the piperazinyl radical advantageously takes place by the action of formaldehyde in the presence of formic acid. The reaction is generally carried out in an aqueous medium at a temperature of between 90° and 100° C.

According to the invention, the benzo[b][1,8]naphthyridine derivatives of general formula (I) can also be obtained from the corresponding ester of general formula:

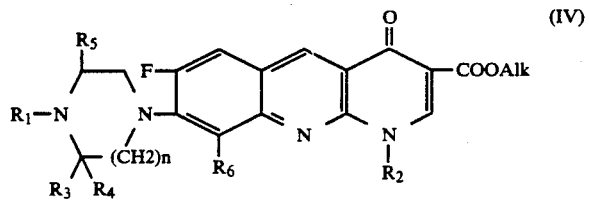

in which $R_1$, $R_2$, $R_3$, $R_4$, $R_5$, $R_6$ and n are defined as above or $R_2$ represents a protected alkylamino radical and Alk represents a straight-chain or branched alkyl radical, containing 1 to 4 carbon atoms, by any known method for obtaining an acid from an ester without touching the remainder of the molecule, followed, where appropriate, by the removal of the protective group from the alkylamino radical, and/or, if a product of general formula (I) in which R is a hydrogen atom has been obtained and if it is desired to obtain the corresponding product in which R is methyl, by the conversion of the product obtained to a 8-(4-methyl-1-piperazinyl)-benzo[b][1,8]naphthyridine.

The preparation of the acid from the ester generally takes place by acid hydrolysis. The reaction is advantageously carried out in an acetic acid/hydrochloric acid mixture, in sulphuric acid or in methanesulphonic acid at a temperature of between 20° and 100° C. It is also possible to carry out the preparation by saponification in the presence of potassium hydroxide or sodium hydroxide in an aqueous-alcoholic medium at a temperature of between 20° and 80° C.

Where appropriate, the methylation of the piperazinyl radical is carried out as described above.

When $R_2$ represents a protected alkylamino radical, the protective radical can be any amino protective group compatible with the molecule. It is particularly advantageous to choose a protective radical which can be removed simultaneously with the hydrolysis of the ester (for example the formyl radical).

The benzo[b][1,8]naphthyridine derivative of general formula (III) can be obtained from the corresponding ester of general formula:

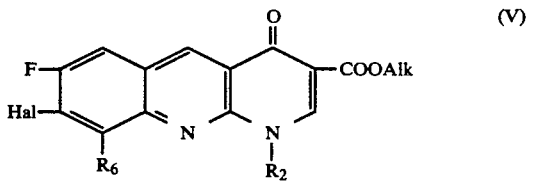

in which Hal, $R_6$ and Alk are defined as above and $R_2$ is defined as above or represents a protected alkylamino radical, by any method known for obtaining an acid from an ester without touching the remainder of the molecule, followed, if appropriate, by the removal of the protective group from the alkylamino radical.

The reaction is carried out, in particular, under the conditions described above for obtaining a product of general formula (I) from an ester of general formula (IV).

The benzo[b][1,8]naphthyridine ester derivative of general formula (V) can be prepared by the action of 3-amino-1,2,4-triazine to obtain a product for which $R_2$ is a hydrogen atom, or by the action of a product of general formula:

in which $R_2$ is alkyl, fluoroalkyl, cycloalkyl, alkoxy or optionally protected alkylamino, on a quinoline derivative of general formula:

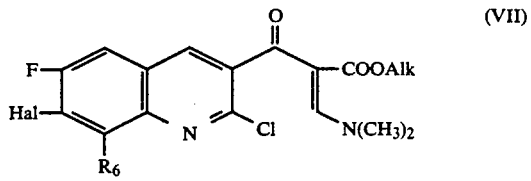

in which $R_6$, Hal and Alk are defined as above, followed by cyclization by the action of an acid acceptor.

In general, the reaction of 3-amino-1,2,4-triazine or of the product of general formula (VI) is carried out in an organic solvent such as an alcohol (ethanol or methanol for example) or a chlorinated solvent (trichloromethane for example) at a temperature of between 10° and 25° C.

The cyclization is carried out in a straight-chain or branched alcohol containing 1 to 4 carbon atoms, at a temperature of between 20° C. and the reflux temperature of the reaction mixture.

The acid acceptor can be chosen, in particular, from the nitrogenous bases (triethylamine for example or an excess of the amine employed) or 1,8-diaza[5.4.0]bicyclo-7-undecene.

The quinoline derivative of general formula (VII) can be obtained from the keto-ester of general formula:

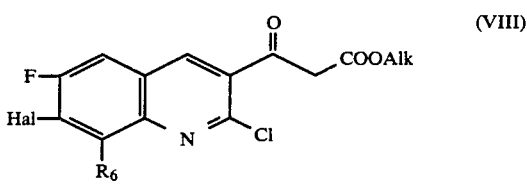

in which $R_6$, Hal and Alk are defined as above, by the action of a N,N-dimethylformamide acetal of general formula:

in which $Alk_1$ is a straight-chain or branched alkyl radical containing 1 to 4 carbon atoms.

The reaction is generally carried out in an organic solvent such as an ester (ethyl acetate for example) at a temperature of between 60° and 75° C.

The keto-ester of general formula (VIII) in which $R_6$ is a hydrogen atom can be obtained from 2,7-dichloro-6-fluoroquinoline-3-carboxylic acid or 2-chloro-6,7-difluoroquinoline-3-carboxylic acid as described below in Examples 1 and 23 or from 7-bromo-2-chloro-6-fluoroquinoline-3-carboxylic acid by analogy with this method. In this case, the 3-bromo-4-fluoroaniline used as starting material can be prepared by the method described by W. B. Austin et al., J. Org. Chem., 46 (11), 2280 (1981).

The keto-ester of general formula (VIII) in which $R_6$ is a fluorine atom can be obtained from 2-chloro-6,7,8-trifluoroquinoline-3-carboxylic acid as described below in Example 25.

The benzo[b][1,8]naphthyridine derivative of general formula (IV) can be obtained from the benzo[b][1,8-]naphthyridine derivative of general formula (V) by substitution of a piperazine derivative of general formula (II).

The reaction is advantageously carried out under the conditions described above for obtaining a product of general formula (I) from a piperazine of general formula (II) and a benzo[b][1,8]naphthyridine of general formula (III).

The piperazine derivatives of general formula (II) can be obtained according to or by analogy with the methods described by:
S. HARRY et al., J. Am. Chem. Soc., 75, 4949 (1963)
G. CIGNARELLA, J. Med. Chem., 7, 241 (1964) or J. Het. Chem., 11, 985 (1974),
J. R. PIPER, J.Org. Chem., 28, 981 (1963),
ISCHIGURO, MATSUMARA, J. Pharm. Soc. Japan, 79, 153 and 302 (1959).

According to the invention, when $R_3$ and $R_4$ are different the benzo[b][1,8]naphthyridine derivatives of general formula (I) represent the isomeric forms. It is understood that these isomers and their mixtures fall within the scope of the present invention.

When it is desired to obtain the isomers of benzonaphthyridine derivatives of general formula (I), the separation of the isomeric forms of the piperazines of general formula (II) is carried out by an method known and compatible with the molecule. By way of example, the separation is carried out by acylation by means of a chiral acid, separation of the isomers by high performance liquid chromatography, followed by deacylation by acid hydrolysis.

The new products according to the present invention and their synthesis intermediates can, if necessary, be purified by physical methods such as crystallization or chromatography.

The products according to the present invention can be converted to metal salts or addition salts with nitrogenous bases by the methods known per se. These salts can be obtained by the action of a metal (for example alkali metal or alkaline earth metal)—containing base, ammonia or an amine on a product according to the invention in an appropriate solvent, such as an alcohol, an ether or water, or by an exchange reaction with a salt of an organic acid. The salt formed precipitates, after concentration of its solution if necessary; it is separated off by filtration, decanting or lyophilization.

The new products according to the invention can also be converted to acid addition salts. The products of general formula (I) obtained in the form of these salts can be liberated and converted to salts of other acids by customary methods.

The following may be mentioned as examples of pharmaceutically acceptable salts: the salts with the alkali metals (sodium, potassium, lithium) or with the alkaline earth metals (magnesium, calcium), the ammonium salt, the salts of nitrogenous bases (ethanolamine, diethanolamine, trimethylamine, triethylamine, methylamine, propylamine, diisopropylamine, N,N-dimethylethanolamine, benzylamine, dicyclohexylamine, N-benzyl-β-phenethylamine, N,N'-dibenzylethylenediamine, diphenylenediamine, benzhydrylamine, quinine, choline, arginine, lysine, leucine, dibenzylamine) and the addition salts with inorganic acids (hydrochlorides, hydrobromides, sulphates, nitrates, phosphates) or organic acids (succinates, fumarates, maleates, p-toluenesulphonates).

The new benzo[b][1,8]naphthyridine derivatives of general formula (I) according to the present invention and their pharmaceutically acceptable salts have particularly valuable antibacterial properties. They display a remarkable in vitro and in vivo activity on Gram-positive germs and, in a general manner, on the germs responsible for the majority of the infections of the upper and lower air passages.

In vitro, the products of general formula (I) have been shown to be active at a concentration of between 0.12 and 50 $\mu$g/cm$^3$ on *Staphylococcus aureus* IP 8203.

In vivo, the products of general formula (I) have been shown to be active against experimental infections of mice with *Staphylococcus aureus* IP 8203 at doses of between 2 and 150 mg/kg administered orally or subcutaneously.

Another valuable characteristic of the products according to the invention is their low toxicity. Their $LD_{50}$ is generally greater than 500 mg/kg when administered subcutaneously to mice.

Products of general formula (I) of particular interest are those in which
$R_1$ represents a hydrogen atom or an alkyl radical containing 1 or 2 carbon atoms which is optionally substituted by a hydroxyl radical,
$R_2$ represents a hydrogen atom or a straight-chain or branched alkyl radical containing 1 to 4 carbon atoms, which is optionally substituted by a fluorine atom,
$R_3$ represents a methyl radical and
$R_4$ and $R_5$, which are different, represent a hydrogen atom or a methyl radical, or
$R_3$ is a hydrogen atom or a methyl radical and $R_4$ and $R_5$ represent hydrogen atoms,
$R_6$ represents a hydrogen or fluorine atom and
n is equal to 1 or 2.

And amongst these products the following are very particularly interesting:
7-fluoro-1-methyl-8-(3-methyl-1-piperazinyl)-4-oxo-1,4-dihydro-benzo[b][1,8]naphthyridine-3-carboxylic acid
1-ethyl-7-fluoro-8-(1-piperazinyl)-4-oxo-1,4-dihydro-benzo[b][1,8]naphthyridine-3-carboxylic acid
1-cyclopropyl-7-fluoro-8-(1-piperazinyl)-4-oxo-1,4dihydro-benzo[b][1,8]naphthyridine-3-carboxylic acid
7,9-difluoro-1-methyl-8-(4-methyl-1-piperazinyl)-4-oxo-1,4-dihydro-benzo[b][!,8]naphthyridine-3-carboxylic acid
8-(3,4-dimethyl-1-piperazinyl)-1-ethyl-7-fluoro-4-oxo-1,4-dihydro-benzo[b][1,8]naphthyridine-3-carboxylic acid.

EXAMPLES

The following examples, given as nonlimiting examples, illustrate the present invention

EXAMPLE 1

A suspension of 3.5 g of 8-chloro-7-fluoro-1-methyl-4-oxo-1,4-dihydro-benzo[b][1,8]naphthyridine-3-carboxylic acid and 4.6 g of 2-methylpiperazine in 40 cm$^3$ of pyridine is heated at a temperature close to 115° C., with stirring, for 13 hours. The reaction mixture is concentrated to dryness under reduced pressure (20 kPa) at 60° C. The residue is twice taken up with 30 cm$^3$ of ethanol and concentrated under reduced pressure under the above conditions. The solid obtained is taken up in 60 cm³ of water and 10 cm³ of 30% aqueous potassium hydroxide solution. The aqueous phase is washed with twice 100 cm³ of trichloromethane, 10.28 g of methanesulphonic acid are added and the aqueous phase is again washed with twice 100 cm³ of trichloromethane. 10 cm³ of 30% aqueous potassium hydroxide solution are added. The precipitate formed is drained and washed with 3 times 10 cm³ of water and twice 10 cm³ of ethanol. 2.7 g of 7-fluoro-1-methyl-8-(3-methyl-1-piperazinyl)-4-oxo-1,4-dihydrobenzo[b][1,8]naphthyridine-3-carboxylic acid are obtained in the form of a yellow solid melting at 360°–363° C.

The 8-chloro-7-fluoro-1-methyl-4-oxo-1,4-dihydrobenzo[b][1,8]naphthyridine-3-carboxylic acid can be prepared in the following manner:

A suspension of 15 g of 8-chloro-3-ethoxycarbonyl-7-fluoro-1-methyl-4-oxo-1,4-dihydro-benzo[b][1,8]naphthyridine in 150 cm³ of acetic acid and 150 cm³ of hydrochloric acid as a 17.5% aqueous solution is heated at a temperature close to 100° C., with stirring, for 4 hours. After cooling to a temperature close to 20° C., the product is drained and washed with twice 150 cm³ of ethanol and then twice 100 cm³ of diethyl ether. 12.7 g of 8-chloro-7-fluoro-1-methyl-4-oxo-1,4-dihydro-benzo[b][1,8]naphthyridine-3-carboxylic acid are obtained in the form of a beige solid which sublimes at 400°–405° C. and is used for the subsequent steps without further purification.

The 8-chloro-3-ethoxycarbonyl-7-fluoro-1-methyl-4-oxo-1,4-dihydro-benzo[b][1,8]naphthyridine is prepared in the following manner:

Methylamine is bubbled into a stirred suspension of 19.3 g of ethyl 2-(2,7-dichloro-6-fluoro-quinoline-3-carbonyl)-3-dimethylaminoacrylate in 250 cm³ of ethanol, kept at between 10° and 15° C., until 16 g of gas have been absorbed. The temperature is allowed to rise to about 20° C., 0.8 g of 1,8-diazabicyclo[5.4.0]undec-7-ene (DBU) is added and the mixture is heated to a temperature close to 75° C. for 2 hours. After cooling to about 20° C., the product is drained and washed with diethyl ether. 15 g of 8-chloro-3-ethoxycarbonyl-7-fluoro-1-methyl-4-oxo-1,4-dihydro-benzo[b][1,8]naphthyridine are obtained in the form of a yellow solid melting at 360°–362° C., which is used for the subsequent steps without further purification.

The ethyl 2-(2,7-dichloro-6-fluoro-quinoline-3-carbonyl)-3-dimethylaminoacrylate is prepared in the following manner:

A suspension of 16.5 g of ethyl 3-(2,7-dichloro-6-fluoro-3-quinolyl)-3-oxopropionate in 160 cm³ of ethyl acetate and 19 cm³ of N,N-dimethylformamide dimethyl acetal is heated at a temperature close to 75° C., with stirring, for 2 hours. The reaction mixture is concentrated to dryness under reduced pressure (20 kPa) at 50° C. The dry extract is taken up in 50 cm³ of diisopropyl ether, drained and washed with twice 10 cm³ of diisopropyl ether. 16.57 g of ethyl 2-(2,7-dichloro-6-fluoro-quinoline-3-carbonyl)-3-dimethylaminoacrylate are obtained in the form of an orange solid melting at 122° C. This product is used for the subsequent steps without further purification.

The ethyl 3-(2,7-dichloro-6-fluoro-3-quinolyl)-3-oxopropionate is prepared in the following manner:

A suspension of 38.75 g of 2,7-dichloro-6-fluoroquinoline-3-carboxylic acid in 410 cm³ of trichloromethane and 24 cm³ of thionyl chloride is heated at a temperature close to 60° C., with stirring, for 6 hours. The solution obtained is concentrated to dryness under reduced pressure (20 kPa) at 50° C. The dry extract is twice taken up in a total of 200 cm³ of toluene and again concentrated under reduced pressure under the same conditions as above. The yellow solid obtained, which melts at 124° C., is dissolved in 230 cm³ of anhydrous tetrahydrofuran. The solution obtained is introduced dropwise, with stirring, in the course of 30 minutes, at between 5° and 10° C., into 200 cm³ of a solution of magnesium chelate in tetrahydrofuran, the preparation of which is described below. The temperature is allowed to rise to 20° C. and the mixture is stirred for 1 hour and a half at this temperature. The solution obtained is introduced dropwise, with vigorous stirring, at a temperature close to 5° C., into 1 liter of 0.5 N sulphuric acid. The temperature of the suspension obtained is allowed to rise to 20° C. and the suspension is stirred for a further 2 hours at this temperature. The suspension is extracted with 1 liter of ethyl acetate and the organic and aqueous phases are filtered through diatomaceous silica for filtration, which enables a small amount of insoluble matter to be removed, and the aqueous phase is extracted twice more with 500 cm³ of ethyl acetate. The combined organic extracts are washed with twice 500 cm³ of water, dried over magnesium sulphate and filtered and the filtrate is concentrated to dryness under reduced pressure (20 kPa) at 40° C. The residue is taken up in 100 cm³ of diisopropyl ether at 20° C., drained and washed with twice 30 cm³ of diisopropyl ether. 40.55 g of ethyl 3-(2,7-dichloro-6-fluoro-3-quinolyl)-3-oxopropionate are obtained in the form of a beige solid melting at 112°–114° C. This product is used for the subsequent steps without further purification.

Preparation of the magnesium chelate of ethyl monomalonate:

5 cm³ of absolute ethanol, 0.2 cm³ of tetrachloromethane and 2 g of ethyl monomalonate are added progressively to 6.9 g of magnesium turnings. After heating, a solution of 23.8 g of ethyl monomalonate in 450 cm³ of ethanol is added in the course of 15 minutes. The mixture is heated at a temperature close to 78° C. for 20 hours and concentrated under reduced pressure (20 kPa) at 50° C. The residue is taken up in twice 100 cm³ toluene and concentrated under reduced pressure under the same conditions as above. The grey powder obtained is brought into solution by adding anhydrous tetrahydrofuran so as to obtain a total volume of 200 cm³.

The ethyl monomalonate was prepared by the method described by D. S. Breslow, E. Baumgarten, C. R. Hauser, J. Am. Chem. Soc., 66, 1287 (1944) and distilled under reduced pressure (boiling point=132° C./2.7 kPa).

The 2,7-dichloro-6-fluoroquinoline-3-carboxylic acid is prepared in the following manner:

A solution of 89.3 g of potassium permanganate in 1.4 liters of water is added in the course of 1 hour and while keeping the temperature between 10° and 14° C. to a stirred suspension, cooled to 10° C., of 69.5 g of 2,7-dichloro-6-fluoro-3-formyl-1,4-dihydroquinoline in 282 cm³ of 2 N aqueous potassium hydroxide solution and 282 cm³ of water. The temperature is allowed to rise to about 20° C. and the mixture is stirred for a further 30 minutes at this temperature. 26 g of sodium dithionite are added, the mixture is stirred for 10 minutes at a temperature close to 20° C. and filtered through diatomaceous silica for filtration and the filter cake is washed with twice 250 cm³ of water. The filtrate and the aqueous washing phases are combined and 90 cm³ of a 35% aqueous solution of hydrochloric acid are added. The precipitate formed is extracted with 4 times 500 cm³ of ethyl acetate. The combined organic extracts are washed with 3 times 500 cm³ of water, dried over magnesium sulphate, filtered and concentrated under reduced pressure (20 kPa) at 50° C. The residue is taken up in 350 cm³ of diethyl ether, drained and washed with twice 200 cm³ of diethyl ether. 45 g of 2,7-dichloro-6-fluoroquinoline-3-carboxylic acid are obtained in the form of a beige solid melting at 230° C. which is used for the subsequent steps without further purification.

The 2,7-dichloro-6-fluoro-3-formyl-1,4-dihydroquinoline was prepared in the following manner:

55.6 cm³ of phosphoryl chloride are added in the course of 30 minutes, with stirring, at between 10° and 15° C., to a mixture of 250 cm³ of trichloromethane and 54 cm³ of dimethylformamide and the mixture is stirred for 1 hour at a temperature close to 20° C. 52 g of 7-chloro-6-fluoro-3,4-dihydrocarbostyril are added progressively, with vigorous stirring, in the course of 10 minutes, at about 20° C. to the solution obtained. The suspension obtained is heated to a temperature close to 60° C. and is kept at this temperature for a further 2 hours, with stirring. The reaction mixture is concentrated under reduced pressure (20 kPa) at 50° C. until a pasty mixture is obtained. A mixture of 250 cm³ of water and 250 g of crushed ice is added, with vigorous stirring. The solid obtained is drained at about 5° C. and washed with 4 times 125 cm³ of water at 5° C. The moist product obtained and 58 g of sodium acetate are added simultaneously, in the course of 1 to 500 cm³ of water at 90° C. in such a way as to maintain the pH at about 6. The mixture is stirred for a further 15 minutes at 90° C., the temperature is allowed to fall to about 50° C. and the product is drained at this temperature and washed with 3 times 250 cm³ of water at about 20° C. 54.3 g of 2,7-dichloro-6-fluoro-3-formyl-1,4-dihydroquinoline are obtained in the form of a yellow solid melting at 260° C. which is used in this form for the subsequent steps.

The 7-chloro-6-fluoro-3,4-dihydrocarbostyril is prepared in the following manner:

350 g of aluminium chloride are added in the course of 5 minutes, with vigorous stirring, to 174.4 g of 3'-chloro-4'-fluoro-3-(N-chloro)-propionanilide. The solid mixture is heated to about 60° C. in the course of 30 minutes. The temperature rises on its own to about 80° C. and the reaction mixture becomes liquid. It is then heated to 110° C. in the course of 15 minutes and kept at between 110° and 120° C. for 3 hours. The reaction mixture (at about 110° C.) is poured, in the course of 10 minutes, with vigorous stirring, into a mixture of 500 cm³ of 35% hydrochloric acid and 500 g of crushed ice. The temperature is allowed to rise to 20° C. and the product is drained and washed with 6 times 500 cm³ of water.

The moist product is recrystallized from 1.2 liters of ethanol. 108 g of 7-chloro-6-fluoro-3,4-dihydrocarbostyril are obtained in the form of a beige solid melting at 215° C.

The 3'-chloro-4,-fluoro-3-(N-chloro)propionanilide was prepared in the following manner:

A solution of 127 g of 3-chloropropionyl chloride in 200 cm³ of acetone was added, with stirring, in the course of 35 minutes, to a solution, at a temperature close to 55° C., of 291 g of 3-chloro-4-fluoroaniline in 500 cm³ of acetone and the mixture was kept at this temperature for 2 hours. After cooling to about 20° C., the insoluble matter was removed by filtration and washed with twice 200 cm³ of acetone. The filtrate and the combined washings are poured into 2 liters of water and 1 kg of ice, with stirring. The temperature is allowed to rise to about 20° C. and the mixture is extracted with 4 times 500 cm³ of dichloromethane. The combined organic extracts are washed with 3 times 500 cm³ of water, dried over magnesium sulphate, stirred for 15 minutes with 6 g of Norit vegetable charcoal, filtered through diatomaceous silica for filtration and concentrated under reduced pressure (20 kPa) at 50° C. The solid obtained is recrystallized from a mixture of 133 cm³ of cyclohexane and 67 cm³ of diisopropyl ether. 176 g of 3'-chloro-4'-fluoro-3-(N-chloro)propionanilide are obtained in the form of a beige solid melting at 94° C., which is used in this form for the subsequent steps.

EXAMPLE 2

7-Fluoro-1-methyl-4-oxo-8-(1-piperazinyl)-1,4-dihydro-benzo[b][1,8]naphthyridine-3-carboxylic acid is prepared under the conditions of Example 1 but starting from 10 g of 8-chloro-7-fluoro-1-methyl-4-oxo-1,4-dihydro-benzo[b][1,8]naphthyridine-3-carboxylic acid and 28 g of piperazine in 100 cm³ of pyridine. 5.5 g of 7-fluoro-1-methyl-4-oxo-8-(1-piperazinyl)-1,4-dihydrobenzo[b][1,8]naphthyridine-3-carboxylic acid melting at 370°–375° C.

EXAMPLE 3

7-Fluoro-1-methyl-8-(4-methyl-1-piperazinyl)-4-oxo-1,4-dihydro-benzo[b][1,8]naphthyridine-3-carboxylic acid is prepared under conditions analogous to Example 1 but starting from 5 g of 8-chloro-7-fluoro-1-methyl-4-oxo-1,4-dihydro-benzo[b][1,8]naphthyridine-3-carboxylic acid and 16 g of 1-methylpiperazine in 50 cm³ of pyridine. After concentrating the reaction mixture under reduced pressure, 25 cm³ of acetic acid are added to the residue, which is suspended in 100 cm³ of water. A very small amount of insoluble matter is removed by filtration through diatomaceous silica for filtration. 200 cm³ of 3 N aqueous potassium hydroxide solution are added to the filtrate and a very small amount of insoluble matter is again removed by filtration through diatomaceous silica for filtration. 5 cm³ of acetic acid are added to the filtrate. The precipitate formed is drained and washed with 3 times 50 cm³ of water. After recrystallizing twice from 17 cm³ of dimethylformamide each time, 3.2 g of 7-fluoro-1-methyl-8-(4-methyl-1-piperazinyl)-4-oxo-1,4-dihydro-benzo[b][1,8]-naphthyridine-3-carboxylic acid are obtained in the form of a yellow solid melting at 356° C.

EXAMPLE 4

8-(4-Ethyl-1-piperazinyl)-7-fluoro-1-methyl-4-oxo-1,4-dihydro=benzo[b][1,8]naphthyridine-3-carboxylic acid is prepared under the conditions described below in Example 5 but starting from 1.85 g of 8-chloro-7-fluoro-1-methyl-4-oxo-1,4-dihydro-benzo[b][1,8]naphthyridine-3-carboxylic acid and 2.75 g of 1-ethylpiperazine in 20 cm³ of pyridine. 1.3 g of 8-(4-ethyl-1-piperazinyl)-7-fluoro-1-methyl-4-oxo-1,4-dihydrobenzo[b][1,8]naphthyridine-3-carboxylic acid are obtained in the form of a yellow solid melting at 285°–286° C.

EXAMPLE 5

7-Fluoro-8-[4-(2-hydroxyethyl)-1-piperazinyl]-1-methyl-4-oxo-1,4-dihydro-benzo[b][1,8]naphthyridine- 3-carboxylic acid is prepared under the conditions of Example 1 but starting from 1.6 g of 8-chloro-7-fluoro-1-methyl-4-oxo-1,4-dihydro-benzo[b][1,8]naphthyridine-3-carboxylic acid and 6.8 g of 1-(2-hydroxyethyl)-piperazine in 16 cm³ of pyridine. After concentrating the reaction mixture to dryness under reduced pressure, the residue is taken up in 50 cm³ of water. The mixture is brought to pH 6.9 by adding 0.4 cm³ of acetic acid. The precipitate obtained is drained, washed with twice 10 cm³ of water and recrystallized twice from 10 cm³ of dimethyl-formamide. 1.1 g of 7-fluoro-8-[4-(2-hydroxyethyl)-1-piperazinyl]-1-methyl-4-oxo-1,4-dihydro-benzo[b]1,8]naphthyridine-3-carboxylic acid are obtained in the form of a yellow solid melting at 275°–276° C.

EXAMPLE 6

8-(3,5-Dimethyl-1-piperazinyl)-7-fluoro-1-methyl-4-oxo-1,4-dihydro-benzo[b][1,8]naphthyridine-3-carboxylic acid is prepared under the conditions of Example 3 but starting from 1.7 g of 8-chloro-7-fluoro-1-methyl-4-oxo-1,4-dihydro-benzo[b][1,8]naphthyridine-3-carboxylic acid and 2.5 g of 2,6-dimethylpiperazine in 20 cm³ of pyridine. 1.1 g of 8-(3,5-dimethyl-1-piperazinyl)-7-fluoro-1-methyl-4-oxo-1,4-dihydrobenzo[b][1,8]naphthyridine-3-carboxylic acid hemihydrate are obtained in the form of a yellow solid melting at 294°–295° C.

EXAMPLE 7

1-Ethyl-7-fluoro-8-(1-piperazinyl)-4-oxo-1,4-dihydro-benzo[b][1,8]naphthyridine-3-carboxylic acid is prepared under the conditions of Example 5, but starting from 1.6 g of 8-chloro-1-ethyl-7-fluoro-4-oxo-1,4-dihydro-benzo[b][1,8]naphthyridine-3-carboxylic acid and 4.3 g of piperazine in 20 cm³ of pyridine. After recrystallizing 3 times from, in total, 300 cm³ of dimethylformamide, 0.94 g of 1-ethyl-7-fluoro-8-(1-piperazinyl)-4-oxo-1,4-dihydro-benzo[b][1,8]naphthyridine-3-carboxylic acid trihydrate is obtained in the form of a yellow solid melting at 320°–322° C.

8-Chloro-1-ethyl-7-fluoro-4-oxo-1,4-dihydrobenzo[b][1,8]naphthyridine-3-carboxylic acid is prepared under the conditions of Example 1 but starting from 10.5 g of 8-chloro-7-fluoro-3-ethoxycarbonyl-1-ethyl-4-oxo-1,4-dihydro-benzo[b][1,8]naphthyridine. 9.3 g of 8-chloro-1-ethyl-7-fluoro-4-oxo-1,4-dihydrobenzo[b][1,8]naphthyridine-3-carboxylic acid are obtained in the form of a beige solid melting at 380° C., which is used for the subsequent steps without further purification.

The 8-chloro-3-ethoxycarbonyl-1-ethyl-7-fluoro-4-oxo-1,4-dihydro-benzo[b][1,8]naphthyridine is prepared in the following manner:

16 g of ethylamine are added, in the course of 5 minutes, at between 10° and 15° C., to a stirred suspension of 13.5 g of ethyl 2-(2,7-dichloro-6-fluoroquinoline-3-carbonyl)-3-dimethylaminoacrylate in 135 cm³ of ethanol, the temperature is allowed to rise to about 20° C., 0.5 g of DBU is added and the mixture is heated, with stirring, for 2 hours at a temperature close to 75° C. After cooling to a temperature close to 20° C., the precipitate is drained and washed with twice 100 cm³ of ethanol and twice 100 cm³ of diethyl ether. 10.4 g of 8-chloro-3-ethoxycarbonyl-1-ethyl-7-fluoro-4-oxo-1,4-dihydro-benzo[b][1,8]naphthyridine are obtained in the form of a yellow solid melting at 300°–301° C., which is used for the subsequent steps without further purification.

EXAMPLE 8

1-Ethyl-7-fluoro-8-(4-methyl-1-piperazinyl)-4-oxo-1,4-dihydro-benzo[b][1,8]naphthyridine-3-carboxylic acid is prepared under the conditions of Example 5 but starting from 1.6 g of 8-chloro-1-ethyl-7-fluoro-4-oxo-1,4-dihydro-benzo[b][1,8]naphthyridine-3-carboxylic acid and 4.5 g of 4-methylpiperazine in 16 cm³ of pyridine. After recrystallizing 4 times from, in total, 120 cm³ of dimethylformamide, 1.2 g of 1-ethyl-7-fluoro-8-(4-methyl-1-piperazinyl)-4-oxo-1,4-dihydrobenzo[b][1,8]naphthyridine-3-carboxylic acid are obtained in the form of a yellow solid melting at 285°–286° C. solvated with 1% of water.

EXAMPLE 9

1-Ethyl-7-fluoro-8-(3-methyl-1-piperazinyl)-4-oxo-1,4-dihydro-benzo[b][1,8]naphthyridine-3-carboxylic acid is prepared under the conditions of Example 1 but starting from 2.1 g of 8-chloro-1-ethyl-7-fluoro-4-oxo-1,4-dihydro-benzo[b][1,8]naphthyridine-3-carboxylic acid, 20 cm³ of pyridine and 2.4 g of 2-methylpiperazine. After taking up in ethanol and concentrating to dryness under reduced pressure (20 kPa at 50° C.), the solid residue is taken up in 20 cm³ of water and 10 cm³ of 2 N potassium hydroxide solution. The aqueous solution obtained is washed with twice 20 cm³ of trichloromethane, 10 cm³ of acetic acid are added and the mixture is again washed with twice 40 cm³ of trichloromethane. 23 cm³ of 4.5 N potassium hydroxide solution are added and the suspension obtained is heated to a temperature close to 90° C. After cooling to a temperature close to 20° C., the precipitate is drained and washed with 3 times 10 cm³ of water and twice 10 cm³ of ethanol. After recrystallizing twice from 120 cm³ of dimethylformamide each time, 1.7 g of 1-ethyl-7-fluoro-8-(3-methyl-1-piperazinyl)-4-oxo-1,4-dihydrobenzo[b][1,8]naphthyridine-3-carboxylic acid are obtained in the form of a yellow solid melting at 310°–312° C.

EXAMPLE 10

1-Ethyl-8-(4-ethyl-1-piperazinyl)-7-fluoro-4-oxo-1,4-dihydro-benzo[b][1,8]naphthyridine-3-carboxylic acid is prepared under the conditions of Example 5 but starting from 1.6 g of 8-chloro-1-ethyl-7-fluoro-4-oxo-1,4-dihydro-benzo[b][1,8]naphthyridine-3-carboxylic acid and 2.3 g of 1-ethylpiperazine in 16 cm³ of pyridine. 1.4 g of 1-ethyl-8-(4-ethyl-1-piperazinyl)-7-fluoro-4-oxo-1,4-dihydro-benzo[b][1,8]naphthyridine-3-carboxylic acid are obtained in the form of a yellow solid melting at 287°–288° C., solvated by 1.6% of water.

EXAMPLE 11

1-Ethyl-7-fluoro-8-[4-(2-hydroxyethyl)-1piperazinyl]-4-oxo-1,4-dihydro-benzo[b][1,8]naphthyridine-3-carboxylic acid is prepared under the conditions of Example 5 but starting from 1.6 g of 8-chloro-1-ethyl-7-fluoro-4-oxo-1,4-dihydro-benzo[b][1,8]naphthyridine-3-carboxylic acid and 2.6 g of 1-(2-hydroxyethyl)-piperazine in 16 cm³ of pyridine. 1.3 g of 1-ethyl-7-fluoro-8-[4-(2-hydroxyethyl)-1-piperazinyl] 4-oxo-1,4-dihydro-benzo[b][1,8]naphthyridine-3-carboxylic acid are obtained in the form of a yellow solid melting at 264°–265° C.

EXAMPLE 12

7-Fluoro-1-methylamino-4-oxo-8-(1-piperazinyl)-1,4-dihydro-benzo[b][1,8]naphthyridine-3-carboxylic acid is prepared under the conditions of Example 5 but starting from 2.25 g of 8-chloro-7-fluoro-1-methylamino-4-oxo-1,4-dihydro-benzo[b][1,8]naphthyridine-3-carboxylic acid and 2.4 g of piperazine in 30 cm³ of pyridine. After recrystallizing 3 times from, in total, 400 cm³ of dimethylformamide, 0.82 g of 7-fluoro-1-methylamino-4-oxo-8-(1-piperazinyl)-1,4-dihydro-benzo[b][1,8]naphthyridine-3-carboxylic acid is obtained in the form of a deep yellow solid melting at 322-324° C., solvated by 13.6% of dimethylformamide.

The 8-chloro-7-fluoro-1-methylamino-4-oxo-1,4-dihydro-benzo[b][1,8]naphthyridine-3-carboxylic acid can be prepared under the following conditions:

A suspension of 16.4 g of 8-chloro-3-ethoxycarbonyl-7-fluoro-1-(N-formyl-N-methylamino)-4-oxo-1,4-dihydro-benzo[b][1,8]naphthyridine in 164 cm³ of acetic acid and 164 cm³ of an aqueous 17.5% hydrochloric acid solution is heated at a temperature close to 100° C., with stirring, for 4 hours. After cooling to a temperature close to 10° C., 165 cm³ of 30% slaked lime is added at between 10° and 20° C. The product is drained and washed with 3 times 150 cm³ of water, 3 times 150 cm³ of ethanol and 3 times 150 cm³ of diethyl ether. 13.64 g of 8-chloro-7-fluoro-1-methylamino-4-oxo-1,4-dihydro-benzo[b][1,8]naphthyridine-3-carboxylic acid are obtained in the form of a yellow solid melting at 354°-356° C., which is used for the subsequent steps without further purification.

The 8-chloro-3-ethoxycarbonyl-7-fluoro-1-(N-formyl-N-methylamino)-4-oxo-1,4-dihydro-benzo[b][1,8-]naphthpyridine is prepared under the conditions of Example 1 but starting from 19.25 g of ethyl 2-(2,7-dichloro-6-fluoroquinoline-3-carbonyl)-3-dimethylaminoacrylate, 4.05 g of N-formyl-N-methylhydrazine and 1.6 g of DBU in 200 cm³ of ethanol. 16.4 g of 8-chloro-3-ethoxycarbonyl-7-fluoro-1-(N-formyl-N-methyl-amino)-4-oxo-1,4-dihydro-benzo[b][1,8]naphthyridine are obtained in the form of a colorless solid melting at 296°-298° C., which is used for the subsequent steps without further purification.

The N-formyl-N-methylhydrazine can be prepared by the method described by Carl Th. Pedersen, Acta Chem. Scand., 18(9), 2199 (1964).

EXAMPLE 13

7-Fluoro-1-methylamino-8-(4-methyl-1-piperazinyl)-4-oxo-1,4-dihydro-benzo[b][1,8]naphthyridine-3-carboxylic acid is prepared under conditions analogous to Example 1 but starting from 1.93 g of 8-chloro-7-fluoro-1-methylamino-4-oxo-1,4-dihydrobenzo[b][1,8]naphthyridine-3-carboxylic acid, 2.4 g of 1-methylpiperazine and 20 cm³ of pyridine. After recrystallizing twice from 15 cm³ of dimethylformamide each time, 0.9 g of 7-fluoro-1-methylamino-8-(4-methyl-1-piperazinyl)-4-oxo-1,4-dihydro-benzo[b][1,8]naphthyridine-3-carboxylic acid is obtained in the form of a yellow solid melting at 263°-264° C.

EXAMPLE 14

7-Fluoro-1-methylamino-8-(3-methyl-1-piperazinyl)-4-oxo-1,4-dihydro-benzo[b][1,8]naphthyridine-3-carboxylic acid is prepared under the conditions of Example 5 but starting from 3.2 g of 8-chloro-7-fluoro-1-methylamino-4-oxo-1,4-dihydro-benzo[b][1,8]naphthyridine-3-carboxylic acid and 4 g of 2-methylpiperazine in 40 cm³ of pyridine. The crude product obtained is taken up in 30 cm³ of water and 7 cm³ of 2 N aqueous potassium hydroxide solution. A very small amount of insoluble matter is removed by filtration through diatomaceous silica. The filtrate is washed with twice 20 cm³ of diethyl ether and the product is then precipitated by adding 3.5 cm³ of 4 N methanesulphonic acid. The precipitate obtained is drained and washed with 3 times 20 cm³ of water and 3 times 20 cm³ of ethanol 2.2 g of 7-fluoro-1-methylamino-8-(3-methyl-1-piperazinyl)-4-oxo-1,4-dihydro-benzo[b][1,8]naphthyridine-3-carboxylic acid are obtained in the form of a deep yellow solid melting at 343°-345° C., solvated by 3.7% of water.

EXAMPLE 15

1-Cyclopropyl-7-fluoro-4-oxo-8-(1-piperazinyl)-1,4-dihydro-benzo[b][1,8]naphthyridine-3-carboxylic acid is prepared under the conditions of Example 5 but starting from 1 g of 8-chloro-1cyclopropyl-7-fluoro-4-oxo-1,4-dihydro-benzo[b][1,8]naphthyridine-3-carboxylic acid and 2.6 g of piperazine in 10 cm³ of pyridine. 0.6 g of 1-cyclopropyl-7-fluoro-4-oxo-8-(1-piperazinyl)-1,4-dihydro-benzo[b][1,8]naphthyridine-3-carboxylic acid dihydrate is obtained in the form of a yellow solid melting at 342°-343° C.

8-Chloro-1-cyclopropyl-7-fluoro-4-oxo-1,4-dihydrobenzo[b][1,8]naphthyridine-3-carboxylic acid is prepared under the conditions of Example 1 but starting from 6.1 g of 8-chloro-1-cyclopropyl-3-ethoxycarbonyl-7-fluoro-4-oxo-1,4-dihydro-benzo[b][1,8]naphthyridine. 4.85 g of 8-chloro-1-cyclopropyl-7-fluoro-4-oxo-1,4-dihydro-benzo[b][1,8]naphthyridine-3-carboxylic acid are obtained in the form of a yellow solid melting at 330° C., which is used for the subsequent steps without further purification The 8-chloro-1-cyclopropyl-3-ethoxycarbonyl-7-fluoro-4-oxo-1,4-dihydro-benzo[b][1,8]naphthyridine is prepared under the following conditions:

A solution of 20.6 g of ethyl 2-(2,7-dichloro-6-fluoroquinoline-3-carbonyl)-3-dimethylaminoacrylate and 6 g of cyclopropylamine in 100 cm³ of trichloromethane is stirred at a temperature close to 20° C. for 24 hours. The reaction mixture is concentrated under reduced pressure (20 kPa) at 50° C. The residue is taken up in 180 cm³ of ethanol and 10 g of DBU and the solution obtained is heated at a temperature close to 78° C. for 4 hours. After cooling to a temperature close to 20° C., the precipitate obtained is drained and washed with twice 60 cm³ of ethanol 13.65 g of 8-chloro-1-cyclopropyl-3-ethoxycarbonyl-7-fluoro-4-oxo-1,4-dihydro-benzo[b][1,8]naphthyridine are obtained in the form of a pale yellow solid melting at 256° C., which is used for the subsequent steps without further purification.

EXAMPLE 16

1-Cyclopropyl-7-fluoro-8-(4-methyl-1-piperazinyl)-4-oxo-1,4-dihydro-benzo[b][1,8]naphthyridine-3-carboxylic acid is prepared under the conditions of Example 5 but starting from 1 g of 8-chloro-1-cyclopropyl-7-fluoro-4-oxo-1,4-dihydro-benzo[b][1,8]naphthyridine-3-carboxylic acid and 3 g of 1-methylpiperazine in 10 cm³ of pyridine. After recrystallizing from 10 cm³ of dimethylformamide, 0.63 g of 1-cyclopropyl-7-fluoro-8-(4-methyl-1-piperazinyl)-4-oxo-1,4-dihydro-benzo[b][1,8-]naphthyridine-3-carboxylic acid is obtained in the form of a yellow solid melting at 250° C.

EXAMPLE 17

1-Cyclopropyl-7-fluoro-8-(3-methyl-1-piperazinyl)-4-oxo-1,4-dihydro-benzo[b][1,8]naphthyridine-3 -carboxylic acid is prepared under the conditions of Example 1 but starting from 1 g of 8-chloro-1-cyclopropyl-7-fluoro-4-oxo-1,4-dihydro-benzo[b][1,8]naphthyridine-3-carboxylic acid and 3 g of 2-methylpiperazine in 10 cm$^3$ of pyridine. The pure product is obtained after a supplementary purification by recrystallization from 200 cm$^3$ of dimethylformamide. 0.5 g of 1-cyclopropyl-7-fluoro-8-(3-methyl-1-piperazinyl)-4-oxo-1,4-dihydro-benzo[b][1,8]naphthyridine-3-carboxylic acid hemihydrate is obtained in the form of a yellow solid melting at 343° C.

EXAMPLE 18

1-Cyclopropyl-8-(4-ethyl-1-piperazinyl)-7-fluoro-4-oxo-1,4-dihydro-benzo[b][1,8]naphthyridine-3-carboxylic acid is prepared under the conditions of Example 5 but starting from 2 g of 8-chloro-1-cyclopropyl-7-fluoro-4-oxo-1,4-dihydro-benzo[b][1,8]naphthyridine-3-carboxylic acid and 2.74 g of 1-ethylpiperazine in 20 cm$^3$ of pyridine. The pure product is isolated after a first recrystallization from 105 cm$^3$ of ethanol containing 25% of dimethylformamide followed by a second recrystallization from 75 cm$^3$ of ethanol containing 50% of dimethylformamide. 0.67 g of 1-cyclopropyl-8-(4-ethyl-1-piperazinyl)-7-fluoro-4-oxo-1,4-dihydro-benzo[b][1,8]naphthyridine-3-carboxylic acid is obtained in the form of a yellow-green solid melting at 254° C.

EXAMPLE 19

1-Cyclopropyl-7-fluoro-8-[4-(2-hydroxyethyl)-1-piperazinyl]-4-oxo-1,4-dihydro-benzo[b][1,8]naphthyridine-3-carboxylic acid is prepared under conditions analogous to Example 5 but starting from 4 g of 8-chloro-1-cyclopropyl-7-fluoro-4-oxo-1,4-dihydrobenzo[b][1,8]naphthyridine-3-carboxylic acid and 6.2 g of 1-(2-hydroxyethyl)-piperazine in 40 cm$^3$ of pyridine. The reaction mixture is heated for 22 hours at a temperature close to 115° C. The pure product is isolated after recrystallizing 3 times from 3 times 200 cm$^3$ of ethanol containing 10% of dimethylformamide each time. 0.94 g of 1-cyclopropyl-7-fluoro-8-[4-(2-hydroxyethyl)-1-piperazinyl]-4-oxo-1,4-dihydrobenzo[b][1,8]naphthyridine-3-carboxylic acid is obtained in the form of a yellow solid melting at 255° C.

EXAMPLE 20

7-Fluoro-4-oxo-8-(1-piperazinyl)-1-tert.-butyl-1,4-dihydro-benzo[b][1,8]naphthyridine-3-carboxylic acid is prepared under the conditions of Example 5 but starting from 1.7 g of 8-chloro-7-fluoro-4-oxo-1-tert.-butyl-1,4-dihydro-benzo[b][1,8]naphthyridine-3-carboxylic acid and 4.3 g of piperazine in 20 cm$^3$ of pyridine. The pure product is obtained after a single recrystallization from 20 cm$^3$ of dimethylformamide. 1.25 g of 7-fluoro-4-oxo-8-(1-piperazinyl)-1-tert.-butyl-1,4-dihydro-benzo[b][1,8]naphthyridine-3 -carboxylic acid are isolated in the form of a yellow solid melting at 290° C., solvated by 4.5% of water.

The 8-chloro-7-fluoro-4-oxo-1-tert.-butyl-1,4-dihydro-benzo[b]1,8]naphthyridine-3-carboxylic acid can be prepared in the following manner:

A suspension of 1.88 g of 8-chloro-3-ethoxycarbonyl-7-fluoro-4-oxo-1-tert.-butyl-1,4-dihydrobenzo[b][1,8-]naphthyridine in 10 cm$^3$ of ethanol, 5 cm$^3$ of water and 15 cm$^3$ of 2 N aqueous potassium hydroxide solution is heated at a temperature close to 75° C., with stirring, for one hour. 2 cm$^3$ of acetic acid are added to the solution obtained. The precipitate formed is drained and washed with 3 times 10 cm$^3$ of water and 3 times 10 cm$^3$ of ethanol. After recrystallizing from 50 cm$^3$ of dimethylformamide, 1.7 g of 8-chloro-7-fluoro-4-oxo-1-tert.-butyl-1,4-dihydro-benzo[b][1,8]naphthyridine-3-carboxylic acid are obtained in the form of a yellow solid melting at 398° C.

The 8-chloro-3-ethoxycarbonyl-7-fluoro-4-oxo-1-tert.-butyl-1,4-dihydro-benzo[b][1,8]naphthyridine is prepared under the conditions of Example 17 but starting from 8.86 g of ethyl 2-(2,7-dichloro-6-fluoroquinoline-3-carbonyl)-3-dimethylaminoacrylate and 4.03 g of tert.-butylamine in 45 cm$^3$ of trichloromethane and then in 4.53 g of DBU and 45 cm$^3$ of ethanol 5 g of 8-chloro-3-ethoxycarbonyl-7-fluoro-4-oxo-1-tert.-butyl-1,4-dihydro-benzo[b][1,8]naphthyridine are obtained in the form of a yellow solid melting at 239° C.

EXAMPLE 21

A suspension of 2 g of 8-chloro-7-fluoro-1-methyl-4-oxo-1,4-dihydro-benzo[b][1,8]naphthyridine-3-carboxylic acid in 7.44 g of 2,2-dimethylpiperazine and 20 cm$^3$ of pyridine is heated at a temperature close to 115° C. for 44 hours. The reaction mixture is concentrated to dryness under reduced pressure (20 kPa) at about 60° C. The residue is taken up in 50 cm$^3$ of ethanol and again concentrated, under reduced pressure, under the above conditions. The solid obtained is taken up in 50 cm$^3$ of diethyl ether, drained, washed with twice 30 cm$^3$ of the same solvent and taken up in 120 cm$^3$ of water and 2 g of methanesulphonic acid. A very small amount of insoluble matter is removed by filtering through diatomaceous silica. 2 cm$^3$ of 50% aqueous potassium hydroxide solution are added to the solution obtained. The precipitate formed is drained and washed with 3 times 25 cm$^3$ of water and a single amount of 50 cm$^3$ of ethanol at about 50° C. 1.6 g of 8-(3,3-dimethyl-1-piperazinyl)-7-fluoro-1-methyl-4-oxo-1,4-dihydro-benzo[b][1,8]naphthyridine-3-carboxylic acid are obtained in the form of a yellow solid melting at 362°-365° C., solvated by 4.9% of water.

EXAMPLE 22

A suspension of 1.2 g of 8-chloro-7-fluoro-1-(2-fluoroethyl)-4-oxo-1,4-dihydro-benzo[b][1,8]naphthyridine-3-carboxylic acid in 12 cm$^3$ of pyridine and 3.52 g of 1-methylpiperazine is heated, with stirring, at a temperature close to 110° C. for 6 hours. The reaction mixture is concentrated under reduced pressure (20 kPa) at about 60° C. The residue is taken up in 15 cm$^3$ of water and 2 cm$^3$ of acetic acid. A small amount of insoluble matter is removed by filtration through diatomaceous silica. 6 cm$^3$ of 20% aqueous potassium hydroxide solution are added to the filtrate. A very small amount of insoluble matter is again removed by filtering through diatomaceous silica. 0.6 cm$^3$ of acetic acid is added to the filtrate. The precipitate obtained is drained, washed with twice 5 cm$^3$ of water and twice 5 cm$^3$ of ethanol and recrystallized twice from 10 cm$^3$ of dimethylformamide each time. 0.6 g of 7-fluoro-1-(2-fluoroethyl)-8-(4-methyl-1-piperazinyl)-4-oxo-1,4-dihydro-benzo[b][1,8]naphthyridine-3-carboxylic acid is obtained in the form of a yellow solid melting at 306°-308° C.

8-Chloro-7-fluoro-1-(2-fluoroethyl)-4-oxo-1,4-dihydro-benzo[b][1,8]naphthyridine-3-carboxylic acid was prepared under the conditions of Example 26 but starting from 2.2 g of 8-chloro-3-ethoxycarbonyl-7-fluoro-1-(2-fluoroethyl)-4-oxo-1,4-dihydrobenzo[b][1,8]naphthyridine. After recrystallizing twice from 10 cm$^3$ of dimethylformamide each time, 1.4 g of 8-chloro-7- fluoro-1-(2-fluoroethyl)-4-oxo-1,4-dihydrobenzo[b][1,8-]naphthyridine-3-carboxylic acid are obtained in the form of a yellow solid melting at 310° C.

8-Chloro-3-ethoxycarbonyl-7-fluoro-1-(2-fluoroethyl)-4-oxo-1,4-dihydro-benzo[b][1,8]naphthyridine is prepared in the following manner:

2.7 cm³ of triethylamine are added to a suspension of 1.9 g of 2-fluoroethylamine hydrochloride in 25 cm³ of trichloromethane. 3.5 g of ethyl 2-(2,7-dichloro-6-fluoroquinoline-3-carbonyl)-3-dimethylaminoacrylate are added to the solution obtained at about 20° C. After stirring at this temperature for 16 hours, the solution is concentrated to dryness under reduced pressure (20 kPa) at about 50° C. The residue is taken up in 20 cm³ of ethanol and 3 cm³ of triethylamine and heat at about 75° C., with stirring, for 2 hours. After cooling to about 20° C. the insoluble matter is drained and washed with twice 10 cm³ of ethanol and twice 10 cm³ of diisopropyl ether. 1.9 g of 8-chloro-3-ethoxycarbonyl-7-fluoro-1-(2-fluoro-ethyl)-4-oxo-1,4-dihydro-benzo[b][1,8]naphthyridine are obtained in the form of a yellow solid melting at 268° C., which is used for the subsequent steps without further purification.

EXAMPLE 23

A suspension of 2 g of 7,8-difluoro-1-methoxy-4-oxo-1,4-dihydrobenzo[b][1,8]naphthyridine-3-carboxylic sulphoxide is stirred for 15 minutes at a temperature close to 40° C. After cooling to about 20° C., the reaction mixture is poured into 150 cm³ of water and 27.75 cm³ of 2 N methanesulphonic acid are added. A very small amount of insoluble matter is removed by filtering through diatomaceous silica. 15 cm³ of 2 N aqueous potassium hydroxide solution are added to the solution obtained. The precipitate formed is drained, washed with 3 times 15 cm³ of water and taken up in 100 cm³ of dimethylformamide and the mixture is heated, with stirring, for 10 minutes at a temperature close to 150° C. The suspension is cooled to about 100° C.; the insoluble matter is drained and taken up in 100 cm³ of ethanol and the mixture is heated at a temperature close to 75° C. for 1 hour. The insoluble matter is drained at about 50° C. and washed with 40 cm³ of the same solvent at the same temperature as above. 1.8 g of 7-fluoro-1-methoxy-4-oxo-8-(1-piperazinyl)-1,4-dihydrobenzo[b][1,8]naphthyridine-3-carboxylic acid are obtained in the form of a brown solid melting at 298°-300° C., solvated by 2.4% of water.

The 7,8-difluoro-1-methoxy-4-oxo-1,4-dihydrobenzo[b][1,8]naphthyridine-3-carboxylic acid is prepared under the following conditions:

A suspension of 2.78 g of 3-ethoxycarbonyl-7,8-difluoro-1-methoxy-4-oxo-1,4-dihydrobenzo[b][1,8-]naphthyridine in 30 cm³ of 17.5% of hydrochloric acid and 30 cm³ of acetic acid is heated at a temperature close to 100° C. for 1 hour. After cooling to about 20° C., the reaction mixture is poured into 100 cm³ of water. The precipitate formed is drained and washed with 3 times 30 cm³ of water and twice 5 cm³ of ethanol. After recrystallizing once from 100 cm³ of dimethylformamide containing 20% of ethanol, 2.03 g of 7,8-difluoro-1-methoxy-4-oxo-1,4-dihydrobenzo[b][1,8]naphthyridine-3-carboxylic acid are obtained in the form of a yellow solid melting at 325°-327° C.

The 3-ethoxycarbonyl-7,8-difluoro-1-methoxy-4-oxo-1,4-dihydro-benzo[b][1,8]naphthyridine is prepared under the following conditions:

2.13 g of triethylamine are added to a suspension of 1.7 g of methoxylamine hydrochloride in 40 cm³ of trichloromethane. After stirring for 15 minutes at a temperature close to 20° C., 3.69 g of ethyl 2-(2-chloro-6,7-difluoroquinoline-3-carbonyl)-3dimethylaminoacrylate are added to the solution obtained and the mixture is stirred for 4 hours and a half at about 20° C. The reaction mixture is concentrated to dryness under reduced pressure (20 kPa) at a temperature close to 50° C. The residue is taken up in 70 cm³ of ethanol and 3.6 g of triethylamine and the mixture is heated for 30 minutes at a temperature close to 75° C. After cooling to about 20° C., the precipitate obtained is drained and washed with 3 times 30 cm³ of ethanol. 2.67 g of 3-ethoxycarbonyl-7,8-difluoro-1-methoxy-4-oxo-1,4-dihydro-benzo[b][1,8]naphthyridine are obtained in the form of a pale yellow solid melting at 266°-268° C.

The ethyl 2-(2-chloro-6,7-difluoroquinoline3-carbonyl)-3-dimethylaminoacrylate is prepared in the following manner:

A suspension of 6.17 g of ethyl 3-(2-chloro-6,7-difluoro-3-quinolyl)-3-oxopropionate in 7.15 g of N,N-dimethylformamide dimethyl acetal and 60 cm³ of ethyl acetate is heated at a temperature close to 75° C. for 1 hour 15 minutes. The reaction mixture is concentrated to dryness under reduced pressure (20 kPa) at about 50° C. The residue is taken up in 50 cm³ of diisopropyl ether, drained and washed with 3 times 25 cm³ of the same solvent. 6.65 g of ethyl 2-(2-chloro-6,7-difluoroquinoline-3-carbonyl)-3dimethylaminoacrylate are obtained in the form of an orange solid melting at 140° C.

The ethyl 3-(2-chloro-6,7-difluoro-3-quinolyl)-3-oxopropionate is prepared in the following manner:

A suspension of 14.13 g of 2-chloro-6,7-difluoroquinoline-3-carboxylic acid in 29 cm³ of thionyl chloride and 220 cm³ of trichloromethane is heated at a temperature close to 60° C. for 4 hours. The solution obtained is concentrated to dryness under reduced pressure (20 kPa) at about 60° C. The residue obtained is taken up in 75 cm³ of n-hexane, drained and washed with twice 60 cm³ of the same solvent. The 14.4 g of yellow solid obtained are poured into solution in 115 cm³ of tetrahydrofuran. This solution is introduced dropwise, with stirring, in the course of 35 minutes, at between 5° and 10° C., into 70 cm³ of a solution of magnesium chelate of ethyl monomalonate in tetrahydrofuran, prepared under the conditions described below. The temperature is allowed to rise to about 20° C. and the mixture is stirred for a further 2 hours under these conditions. The solution obtained is introduced dropwise, with stirring, in the course of 30 minutes, at a temperature close to 5° C., into 560 cm³ of 0.5 N sulphuric acid. The temperature of the suspension obtained is allowed to rise to 20° C. and the suspension is then stirred for a further 1 hour and a half at this temperature. It is extracted with 3 times 250 cm³ of ethyl acetate. The combined organic extracts are washed with twice 250 cm³ of water, dried over magnesium sulphate, filtered and concentrated to dryness under reduced pressure (20 kPa) at 50° C. The residue obtained is taken up in 50 cm³ of n-hexane containing 20% of diisopropyl ether, drained, washed with 10 cm³ of the same mixture and recrystallized from 60 cm³ of isopropanol containing 30% of n-hexane. 11.84 g of ethyl 3-(2-chloro-6,7-difluoro-3-quinolyl)-3-oxopropionate are obtained in the form of a cream solid melting at 107° C.

Preparation of the magnesium chelate of ethyl monomalonate:

2 cm³ of absolute ethanol, 0.1 cm³ of tetrachloromethane and 1 g of ethyl monomalonate are added progressively to 2.78 g of magnesium turnings After heating, a solution of 9 g of ethyl monomalonate in 180 cm³ of ethanol is added in the course of 15 minutes. The mixture is heated for 20 hours at a temperature close to 75° C. and concentrated under reduced pressure (20 kPa) at 50° C. The residue is taken up in twice 100 cm³ of toluene and the mixture is concentrated under reduced pressure under the same conditions as above. The grey powder obtained is brought into solution by adding anhydrous tetrahydrofuran in an amount to obtain a total volume of 70 cm³.

The 2-chloro-6,7-difluoroquinoline-3-carboxylic acid was prepared in the following manner:

A solution of 115 g of potassium permanganate in 1.215 liters of water was added in the course of 1 hour, while keeping the temperature between 10° and 14° C., to a stirred suspension, cooled to 10° C., of 70.18 g of 2-chloro-6,7-difluoro-3-formyl-1,4-dihydroquinoline in 970 cm³ of N aqueous potassium hydroxide solution. The temperature is allowed to rise to about 20° C. and the mixture is stirred for a further 30 minutes at this temperature. 38.5 g of sodium dithionite are added, the mixture is stirred for 10 minutes at a temperature close to 20° C. and filtered through diatomaceous silica and the filter cake is washed with 3 times 200 cm³ of water. The filtrate and the aqueous washing phases are combined and 140 cm³ of 35% aqueous hydrochloric acid solution are added. The precipitate formed is extracted with 4 times 800 cm³ of ethyl acetate. The combined organic extracts are washed with twice 500 cm³ of water, dried over magnesium sulphate, filtered and concentrated under reduced pressure (20 kPa) at 50° C. The residue is taken up in 400 cm³ of diethyl ether, drained and washed with twice 200 cm³ of the same solvent. 49.2 g of 2-chloro-6,7-difluoroquinoline-3-carboxylic acid are obtained in the form of a beige solid melting at 232° C., which is used for the subsequent steps without further purification.

The 2-chloro-6,7-difluoro-3-formyl-1,4-dihydroquinoline was prepared in the following manner:

76.9 cm³ of phosphoryl chloride are added in the course of 30 minutes, with stirring, at between 10° and 15° C., to a mixture of 800 cm³ of trichloromethane and 74.35 cm³ of dimethylformamide and the mixture is stirred for 1 hour at a temperature close to 20° C. 65.8 g of 6,7-difluoro-3,4-dihydrocarbostyril are added in the course of 10 minutes, at about 20° C., with vigorous stirring, to the solution obtained. The solution obtained is heated to a temperature close to 60° C. and kept at this temperature for 2 hours. The reaction mixture is concentrated under reduced pressure (20 kPa) at 50° C. until a pasty mixture is obtained. A mixture of 500 g of ice and 500 cm³ of water is added, with vigorous stirring. The solid obtained is drained at about 5° C. and washed with 3 times 300 cm³ of water at 5° C. The moist product obtained and 60 g of sodium acetate are added simultaneously, in the course of 1 hour, to 1.5 liters of water at 90° C., in such a way as to keep the pH at about 6. The mixture is stirred for a further 30 minutes at 90° C., the temperature is allowed to fall to about 50° C. and the product is drained at this temperature and washed with 3 times 300 cm³ of water at about 20° C. 70.18 g of 2-chloro-6,7-difluoro-3-formyl-1,4-dihydroquinoline are obtained in the form of a yellow solid melting at 260° C., which is used in this form for the subsequent steps.

The 6,7-difluoro-3,4-dihydrocarbostyril is obtained in the following manner:

134 g of aluminium chloride are added to 67 g of 3',4'-difluoro-3-(N-chloro)-propionanilide with vigorous stirring and then, after about 2 minutes, a further 135.9 g of 3',4'-difluoro-3-(N-chloro)propionanilide and 272 g of aluminium chloride are added in small fractions in the course of 15 minutes. The temperature rises on its own to about 60° C. and the reaction mixture becomes liquid. It is then heated to 110° C. in the course of 20 minutes and kept at between 110° and 120° C. for 2 hours. The reaction mixture (at about 110° C.) is poured in the course of 10 minutes, with vigorous stirring, into a mixture of 840 cm³ of 35% hydrochloric acid and 1 kg of crushed ice. The temperature is allowed to rise to about 20° C. and the product is drained and washed with 600 cm³ of water, twice 300 cm³ of ethanol at 5° C. and twice 400 cm³ of diethyl ether at about 20° C. 131.58 g of 6,7fluoro- 3,4-dihydrocarbostyril are obtained in the form of a beige solid melting at 216° C., which is used in this form for the subsequent steps.

The 3',4'-difluoro-3-(N-chloro)-propionanilide is prepared in the following manner:

139.16 g of 3-chloro-propionyl chloride are added, with stirring, in the course of 1 hour and a half to a solution of 125 g of 3,4-difluoroaniline in 80 cm³ of pyridine and 1.5 liters of acetone heated to a temperature close to 55° C. and the mixture is kept at this temperature for 1 hour and a half. After cooling to about 20° C., the solution is poured, with stirring, into a mixture of 1 liter of water and 500 g of crushed ice. The temperature is allowed to rise to about 20° C. and the mixture is extracted with 3 times 500 cm³ of dichloromethane. The combined organic extracts are washed with 500 cm³ of N hydrochloric acid and 5 times 500 cm³ of water, dried over magnesium sulphate, filtered and concentrated under reduced pressure (20 kPa) at about 50° C. The solid obtained is taken up in 500 cm³ of n-hexane, drained and washed with twice 100 cm³ of the same solvent. 202.9 g of 3',4'-difluoro-3-(N-chloro)-propionanilide are obtained in the form of a beige solid melting at 76° C., which is used for the subsequent steps without further purification.

EXAMPLE 24

A suspension of 0.93 g of 7,8-difluoro-1-methoxy-4-oxo-1,4-dihydro-benzo[b][1,8]naphthyridine-3-carboxylic acid in 0.6 g of 1-methylpiperazine and 20 cm³ of dimethyl sulphoxide is heated at a temperature close to 80° C. for 5 minutes. After cooling to about 20° C., the reaction mixture is poured into 30 cm³ of water, 1.5 cm³ of 2 N methanesulphonic acid are added and the product is drained and washed with 3 times 5 cm³ of water. After recrystallizing from 30 cm³ of dimethylformamide containing 30% of ethanol, 0.55 g of 7-fluoro-1-methoxy-8-(4-methyl-1-piperazinyl)-4-oxo-1,4-dihydro-benzo[b][1,8]naphthyridine-3-carboxylic acid is obtained in the form of a brown solid melting at 270° C.

EXAMPLE 25

A suspension of 0.47 g of 1-cyclopropyl-7,8-difluoro-4-oxo-1,4-dihydro-benzo[b][1,8]naphthyridine-3-carboxylic acid and 0.6 g of 1-methylpiperazine in 7 cm³ of dimethyl sulphoxide is heated at a temperature close to 80° C. for 15 minutes. The reaction mixture is poured into 25 cm³ of water and 9 cm³ of N hydrochloric acid are added. The solid obtained is drained and washed with 3 times 5 cm³ of water. After recrystallizing once from a mixture of 4.5 cm³ of ethanol and of 4.5 cm³ of dimethylformamide, 0.29 g of 1-cyclopropyl-7-fluoro-8-(4-methyl-1-piperazinyl)-4-oxo-1,4-dihydrobenzo[b][1,8]naphthyridine-3-carboxylic acid is obtained in the form of a yellow solid melting at 250° C..

The 7,8-difluoro-1-methoxy-4-oxo-1,4-dihydrobenzo[b][1,8]naphthyridine-3-carboxylic acid can be prepared in the following manner:

A suspension of 1.95 g of 1-cyclopropyl-3-ethoxycarbonyl-7,8-difluoro-4-oxo-1,4-dihydrobenzo[b][1,8-]naphthyridine in 20 cm³ of 17.5% hydrochloric acid and 20 cm³ of acetic acid is heated at a temperature close to 100° C. for 1 hour 30 minutes. After cooling to about 20° C., the reaction mixture is poured into 100 cm³ of water. The precipitate is drained and washed with 3 times 20 cm³ of water. After recrystallizing once from a mixture of 30 cm³ of dimethylformamide and 30 cm³ of ethanol, 1.31 g of 1-cyclopropyl-7,8-difluoro-4-oxo-1,4-dihydrobenzo[b][1,8]naphthyridine-3-carboxylic acid are obtained in the form of a yellow solid melting at 284°-285° C.

The 1-cyclopropyl-3-ethoxycarbonyl-7,8difluoro-4-oxo-1,4-dihydro-benzo[b][1,8]naphthyridine is prepared in the following manner:

A stirred suspension of 5.27 g of ethyl 2-(2-chloro-6,7-difluoroquinoline-3-carbonyl)-3-cyclopropylaminoacrylate in 2.22 g of 1,8-diazobicyclo[5.4.0]undec-7-ene (DBU) and 120 cm³ of ethanol is heated at a temperature close to 75° C. for 35 minutes. After cooling to about 20° C., the reaction mixture is taken up in 100 cm³ of water and extracted once with 100 cm³ and twice with 50 cm³ of trichloromethane. The combined organic extracts are washed with 3 times 50 cm³ of water, dried over magnesium sulphate, filtered and concentrated under reduced pressure (20 kPa) at a temperature close to 20° C. The dry extract obtained is taken up in 30 cm³ of diisopropyl ether, drained and recrystallized from a mixture of 75 cm³ of ethanol and 75 cm³ of dimethylformamide. 3.57 g of 1-cyclopropyl-3-ethoxycarbonyl-7,8-difluoro-4-oxo-1,4-dihydrobenzo[b][1,8-]naphthyridine are obtained in the form of a yellow solid melting at 229°-230° C.

The ethyl 2-(2-chloro-6,7-difluoroquinoline-3-carbonyl)-3-cyclopropylaminoacrylate is prepared in the following manner:

A solution of 6.25 g of 2-(2-chloro-6,7-difluoroquinoline-3-carbonyl)-3-dimethylaminoacrylate in 2.91 g of cyclopropylamine and 25 cm³ of trichloromethane is stirred for 3 hours at a temperature close to 20° C. The reaction mixture is concentrated under reduced pressure (20 kPa) at a temperature close to 50° C. The dry extract is taken up in 50 cm³ of diisopropyl ether, drained and then washed with 20 cm³ of the same solvent.

5.27 g of ethyl 2-(2-chloro-6,7-difluoroquinoline-3-carbonyl)-3-cyclopropylaminoacrylate are obtained in the form of an orange solid melting at 116°-117° C. This product is used for the subsequent steps without further purification.

EXAMPLE 26

A suspension of 4 g of 7,8,9-trifluoro-1-methyl-4-oxo-1,4-dihydro-benzo[b][1,8]naphthyridine-3-carboxylic acid in 60 cm³ of dimethyl sulphoxide and 3 g of 1-methylpiperazine is heated at 80° C. for 1 hour and a half. After cooling to about 20° C., 150 cm³ of water are added. 18 cm³ of 10% acetic acid are added to the solution obtained. The precipitate formed is drained, washed with 3 times 50 cm³ of water and recrystallized from 50 cm³ of dimethylformamide. 4 g of 7,9-difluoro-1-methyl-8-(4-methyl-1-pip-erazinyl)-4-oxo-1,4-dihydrobenzo[b]1,8]naphthyridine-3-carboxylic acid are obtained in the form of a yellow solid melting at 316° C..

The 7,8,9-trifluoro-1-methyl-4-oxo-1,4-dihydrobenzo[b][1,8]naphthyridine-3-carboxylic acid is prepared in the following manner:

A suspension of 4 g of 3-ethoxycarbonyl-7,8,9-trifluoro-1-methyl-4-oxo-1,4-dihydro-benzo[b][1,8]naphthyridine in 30 cm³ of acetic acid and 30 cm³ of 50% hydrochloric acid is heated at a temperature close to 100° C. for 2 hours. After cooling to about 20° C., 100 cm³ of water are added. The precipitate formed is drained, washed with 3 times 50 cm³ of water and recrystallized from 80 cm³ of dimethylformamide 3.4 g of 7,8,9-trifluoro-1-methyl-4-oxo-1,4-dihydrobenzo[b][1,8-]naphthyridine-3-carboxylic acid are obtained in the form of a colorless solid melting at 350°-352° C.

The 3-ethoxycarbonyl-7,8,9-trifluoro-1-methyl-4-oxo-1,4-dihydro-benzo[b][1,8]naphthyridine is prepared in the following manner:

A solution, at about 5° C., of 10 g of methylamine in 50 cm³ of ethanol is added in the course of 10 minutes, at between 5° and 10° C., to a stirred suspension of 19.3 g of ethyl 2-(2-chloro-6,7,8-trifluoroquinoline-3-carbonyl)-3-dimethylaminoacrylate in 150 cm³ of ethanol kept at a temperature close to 5° C., the mixture is stirred for 1 hour at between 5° and 10° C. and the temperature is allowed to rise to about 20° C. 7.6 g of DBU are added to the solution obtained and the mixture is heated at about 30° C. for 1 hour. After cooling to a temperature close to 20° C., the product is drained and washed with twice 100 cm³ of ethanol and twice 100 cm³ of diisopropyl ether. 13.4 g of 3-ethoxycarbonyl-7,8,9-trifluoro-1-methyl-4-oxo-1,4-dihydro-benzo[b][1,8]naphthyridine are obtained in the form of a yellow solid melting at 320° C., which is used for the subsequent steps without further purification.

The ethyl 2-(2-chloro-6,7,8-trifluoroquinoline-3-carbonyl)-3-dimethylaminoacrylate can be prepared in the following manner:

A suspension of 26.7 g of ethyl 3-(2-chloro-6,7,8-trifluoro-3-quinolyl-)-3-oxopropionate in 270 cm³ of ethyl acetate and 32 cm³ of N,N-dimethylformamide dimethyl acetal is heated at a temperature close to 75° C., with stirring, for 2 hours. The reaction mixture is concentrated to dryness under reduced pressure (20 kPa) at about 50° C. The dry extract is taken up in 175 cm³ of diisopropyl ether, drained and washed with twice 85 cm³ of the same solvent. 19.32 g of ethyl 2-(2-chloro-6,7,8-trifluoroquinoline-3-carbonyl)-3-dimethylaminoacrylate are obtained in the form of an orange solid melting at 118° C., which is used for the subsequent steps without further purification.

The ethyl 3-(2-chloro-6,7,8-trifluoro-3-quinolyl)-3-oxopropionate is prepared in the following manner:

A suspension of 46.3 g of 2-chloro-6,7,8-trifluoroquinoline-3-carboxylic acid in 640 cm³ of trichloromethane and 84 cm³ of thionyl chloride is heated, with stirring, at a temperature close to 60° C. for 6 hours. The solution obtained is concentrated to dryness under reduced pressure (20 kPa) at about 50° C. The dry extract obtained is taken up in 140 cm³ of petroleum ether (40-60), drained and washed with twice 60 cm³ of the same solvent. The 47.61 g of yellow solid obtained are brought into solution in 400 cm³ of tetrahydrofuran. This solution is introduced dropwise, with stirring, in the course of 1 hour and a half, at between 5° and 10° C., into 250 cm³ of a solution of the magnesium chelate of ethyl monomalonate in tetrahydrofuran prepared under the conditions of Example 23. The temperature is allowed to rise to about 20° C. and the mixture is stirred for a further 2 hours under these conditions. The solution obtained is introduced dropwise, with vigorous stirring, in the course of 1 hour, at a temperature close to 5° C., into 1750 cm³ of 0.5 N sulphuric acid. The mixture is stirred for a further 2 hours at this temperature and extracted at about 5° C. with 3 times 600 cm³ of diethyl ether. The combined organic phases are washed with 3 times 500 cm³ of water, dried over magnesium sulphate and concentrated under reduced pressure (20 kPa) at a temperature close to 30° C. The dry extract is taken up in a mixture of 135 cm³ of diisopropyl ether and 15 cm³ of n-hexane, drained at about 5° C. and washed with twice 115 cm³ of the same mixture at the same temperature. 47.4 g of ethyl 3-(2-chloro-6,7,8-trifluoro-3-quinolyl)-3-oxopropionate are obtained in the form of a beige solid melting at 78°–80° C., which is used for the subsequent steps without further purification.

The 2-chloro-6,7,8-trifluoroquinoline-3-carboxylic acid is prepared in the following manner:

A solution of 69.65 g of potassium permanganate in 730 cm³ of water is added in the course of 1 hour, while keeping the temperature between 10° and 14° C., to a stirred suspension, cooled to about 10° C., of 45.7 g of 2-chloro-6,7,8-trifluoro-3-formyl-1,4-dihydroquinoline in 585 cm³ of N potassium hydroxide solution. The mixture is stirred for a further 30 minutes at about 10° C. 12 g of sodium dithionite are added and the mixture is stirred for 10 minutes at a temperature close to 10° C. and filtered through diatomaceous silica and the filter cake is washed with 3 times 400 cm³ of water. The filtrate and the washings are combined and 70 cm³ of a 35% aqueous solution of hydrochloric acid times 500 cm³ of ethyl acetate. The combined organic extracts are dried over magnesium sulphate, filtered and concentrated under reduced pressure (20 kPa) at 50° C. The residue is taken up in a mixture of 100 cm³ of diethyl ether and 100 cm³ of diisopropyl ether, drained and washed with 100 cm³ of the same mixture. 46.43 g of 2-chloro-6,7,8-trifluoroquinoline-3-carboxylic acid are obtained in the form of a colorless solid which decomposes at 225°–230° C. and which is used for the subsequent steps without further purification.

The 2-chloro-6,7,8-trifluoro-3-formyl-1,4-dihydroquinoline is prepared in the following manner:

50 cm³ of phosphoryl chloride are added in the course of 40 minutes, with stirring, at between 5° and 10° C., to a mixture of 525 cm³ of trichloromethane and 49 cm³ of dimethylformamide, the mixture is stirred for 15 minutes at this temperature and the temperature is allowed to rise to about 20° C. 46.8 g of 6,7,8-trifluoro-3,4-dihydrocarbostyril are added progressively in the course of 20 minutes, at about 20° C., with vigorous stirring, to the solution obtained. The mixture is stirred for 30 minutes at a temperature close to 20° C., heated to about 60° C. and kept at this temperature for 2 hours and a half. The reaction mixture is concentrated under reduced pressure (20 kPa) at about 50° C. The oily residue is poured into 500 g of ice, with vigorous stirring. 100 g of sodium acetate are added in small fractions in the course of 30 minutes. The suspension obtained is poured in the course of 15 minutes, with vigorous stirring, into 1 liter of water which has previously been heated to about 90° C. and the mixture is stirred for a further 15 minutes at this temperature. The insoluble matter is drained at about 90° C. and washed with 3 times 250 cm³ of water. 47.7 g of 2-chloro-6,7,8-trifluoro-3-formyl-1,4-dihydroquinoline are obtained in the form of a colorless solid which decomposes at 220° C.

The 6,7,8-trifluoro-3,4-dihydrocarbostyril is prepared in the following manner:

24.35 g of 6,7,8-trifluorocarbostyril in suspension in a mixture of 450 cm³ of ethanol and 150 cm³ of dimethylformamide are hydrogenated, with stirring, at about 50° C., in the presence of 5 g of Raney nickel under a pressure of 1 atmosphere until the absorption of hydrogen has ceased. The W-2 grade Raney nickel used is washed beforehand with 50 cm³ of an aqueous 2% acetic acid solution, twice 50 cm³ of water and 3 times 50 cm³ of ethanol. 250 cm³ of dimethylformamide are added to the reaction mixture and the mixture is filtered at about 50° C. through diatomaceous silica. The filtrate is concentrated under reduced pressure (20 kPa) at about 70° C. The dry extract is taken up in 150 cm³ of water, drained and washed with twice 50 cm³ of water. 23.6 g of 6,7,8-trifluoro-3,4-dihydrocarbostyril are obtained in the form of a light beige solid melting at 217° C., which is used for the subsequent steps without further purification.

The 6,7,8-trifluorocarbostyril is prepared in the following manner:

60.83 g of 4-chloro-6,7,8-trifluorocarbostyril in suspension in 520 cm³ of acetic acid and 38.15 cm³ of triethylamine are hydrogenated under a pressure of 1 atmosphere in the presence of 5.25 g of 10% palladium-on-charcoal until the absorption of hydrogen has ceased, at a temperature close to 25° C. The reaction mixture is then heated to about 40° C. and filtered at this temperature through diatomaceous silica for filtration. The filtrate is concentrated under reduced pressure (20 kPa) at a temperature close to 50° C.. The dry extract is taken up in 400 cm³ of water; the insoluble matter is drained and washed with 4 times 170 cm³ of water, twice 110 cm³ of ethanol and twice 100 cm³ of diisopropyl ether. 48.35 g of 6,7,8-trifluorocarbostyril are obtained in the form of a colorless solid which sublimes at 288° C. and which is used for the subsequent steps without further purification.

The 4-chloro-6,7,8-trifluorocarbostyril is prepared in the following manner:

A suspension of 70.4 g of 4-chloro-2-ethoxy-6,7,8-trifluoroquinoline in 170 cm³ of a 35% aqueous solution of hydrochloric acid, 420 cm³ of acetic acid and 250 cm³ of water is heated, with stirring, at a temperature close to 100° C. for 2 hours and a half. After cooling to about 20° C., the reaction mixture is poured into 1,100 cm³ of water at about 5° C., the mixture is stirred for 15 minutes at this temperature and the insoluble matter is then drained and washed with 3 times 220 cm³ of water. 61 g of 4-chloro-6,7,8-trifluorocarbostyril are obtained in the form of a cream solid melting at 213° C., which is used for the subsequent steps without further purification.

The 4-chloro-2-ethoxy-6,7,8-trifluoroquinoline is prepared in the following manner:

A suspension of 69.5 g of 2-ethoxy-6,7,8-trifluoro-4-hydroxyquinoline in 430 cm³ of phosphoryl chloride is heated, with stirring, at a temperature close to 100° C. for 30 minutes. The solution obtained is concentrated under reduced pressure (20 kPa) at about 60° C. until the volume is 100 cm³. The residue is taken up in 750 cm³ of ethyl acetate; the solution obtained is poured, with stirring, in the course of 10 minutes into a mixture of 400 cm³ of water and 200 g of ice and the mixture is stirred under these conditions for 30 minutes. After separating off the organic extract, the aqueous phase is extracted again with twice 250 cm³ of ethyl acetate. The combined organic extracts are washed with 3 times 250 cm³ of water, dried over magnesium sulphate and concentrated under reduced pressure (20 kPa) at about 40° C. The oily residue obtained is taken up in 370 cm³ of petroleum ether (40–60). After filtering through diatomaceous silica, the filtrate is concentrated to dryness under reduced pressure (20 kPa) at about 30° C. 70.7 g of 4-chloro-2-ethoxy-6,7,8-trifluoroquinoline are obtained in the form of a beige solid melting at 45° C., which is used for the subsequent steps without further purification.

The 2-ethoxy-6,7,8-trifluoro-4-hydroxyquinoline can be prepared in the following manner:

A solution of 122 g of 2,3,4-trifluoro-N-[(1'-ethoxy-2'-ethoxycarbonyl)ethylidene]-aniline in 120 cm³ of phenyl oxide is introduced dropwise, in the course oxide at a temperature close to 250° C. while removing the ethanol formed by distillation. After stirring for 15 minutes at this temperature, the solution is cooled to about 20° C. and 750 cm³ of n-hexane are added. The precipitate formed is drained and washed 3 times with 4-hydroxyquinoline are obtained in the form of a beige solid melting at 171° C., which is used for the subsequent steps without further purification.

The 2,3,4-trifluoro-N-[(1'-ethoxy-2'ethoxycarbonyl)ethylidene]-aniline can be prepared in the following manner:

58.8 g of 2,3,4-trifluoroaniline are added in a single amount, with stirring, to a solution of 90 g of 2-ethoxycarbonyl-1-ethoxy-ethylideneamine hydrochloride in 820 cm³ of ethanol. After stirring for 48 hours at a temperature close to 20° C., the suspension obtained is filtered; the filtrate is concentrated under reduced pressure (20 kPa) at a temperature close to 50° C. The oily residue is taken up in 250 cm³ of water. The mixture obtained is extracted with 3 times 200 cm³ of diethyl ether. The combined organic extracts are washed with 4 times 150 cm³ of water, dried over magnesium sulphate and concentrated under reduced pressure (20 kPa) at about 30° C. 122 g of 2,3,4-trifluoro-N-[(1'-ethoxy-2'-ethoxycarbonyl)ethylidene]-aniline are obtained in the form of a yellow oil which is used for the subsequent steps without further purification.

The 2-ethoxycarbonyl-1-ethoxy-ethylideneamine hydrochloride was prepared by the method described by A. Pinner, et al., Ber. Dtsch. Chem. Ges., 28, 478 (1895).

EXAMPLE 27

A suspension of 2 g of 6,7,8-trifluoro-1-methoxy-4-oxo-1,4-dihydro-benzo[b][1,8]naphthyridine-3-carboxylic acid and 2.8 g of piperazine in 40 cm³ of dimethyl sulphoxide is heated, with stirring, at about 50° C. for 45 minutes. After cooling to a temperature close to 20° C., the suspension obtained is poured into 100 cm³ of water to which 9.22 g of methanesulphonic acid has been added. A small amount of insoluble matter is removed by filtering through diatomaceous silica. 32 cm³ of 2 N aqueous potassium hydroxide solution are added to the filtrate. The precipitate obtained is drained, washed with 3 times 50 cm³ of water and recrystallized from 80 cm³ of dimethylformamide. 1.4 g of 7,9-difluoro-1-methoxy-4-oxo-8-(1-piperazinyl)-1,4-dihydrobenzo[b][1 8]naphthyridine-3-carboxylic acid are obtained in the form of a yellow solid melting at 305°–308° C.

The 6,7,8-trifluoro-1-methoxy-4-oxo-1,4-dihydrobenzo[b][1,8]naphthyridine-3-carboxylic acid was prepared under the conditions of Example 25 but starting from 9 g of 3-ethoxycarbonyl-6,7,8-trifluoro-1-methoxy-4-oxo-1,4-dihydro-benzo[b][1,8]naphthyridine. 7.7 g of 6,7,8-trifluoro-1-methoxy-4-oxo-1,4-dihydrobenzo[b][1,8-]naphthyridine-3-carboxylic acid are obtained in the form of a beige solid melting at 322° C.

The 3-ethoxycarbonyl-6,7,8-trifluoro-1-methoxy-4-oxo-1,4-dihydro-benzo[b][1,8]naphthyridine was prepared under the following conditions:

8.7 cm³ of triethylamine are added to a suspension of 5.1 g of methylhydroxylamine hydrochloride in 120 cm³ of trichloromethane. 7.8 g of ethyl 2-(2-chloro-6,7,8-trifluoroquinoline-3-carbonyl)-3-dimethylaminoacrylate are added, at about 20° C., to the solution obtained. After stirring for 2 hours at this temperature, the solution is concentrated to dryness under reduced pressure (20 kPa) at about 50° C. The residue obtained is taken up in 150 cm³ of ethanol and 10 cm³ of triethylamine and the mixture is heated, with stirring, for 30 minutes. After cooling to about 20° C., the insoluble matter is drained and washed with 3 times 50 cm³ of ethanol and twice 50 cm³ of diisopropyl ether. After recrystallizing from 120 cm³ of dimethylformamide, 9 g of 3-ethoxycarbonyl-6,7,8-trifluoro-1-methoxy-4-oxo-1,4-dihydro-benzo[b][1,8]naphthyridine are obtained in the form of a yellow solid melting at 298°–300° C.

EXAMPLE 28

A solution of 1.15 g of 7-fluoro-1-methyl-8-(3-methyl-1-piperazinyl)-4-oxo-1,4-dihydrobenzo[b][1,8]naphthyridine-3-carboxylic acid in 1.35 cm³ of 98% formic acid and 3.25 cm³ of a 30% aqueous formaldehyde solution is heated at a temperature close to 100° C. for 2 hours. The reaction mixture is concentrated under reduced pressure (20 kPa) at 50° C. and 5 cm³ of water are then added, the solution obtained is brought to pH 7 by adding 0.5 cm³ of 2 N aqueous potassium hydroxide solution and heated at a temperature close to 100° C. for 2 minutes. The product, which crystallizes, is drained at 20° C. and washed with twice 10 cm³ of water. The crude product obtained is recrystallized twice from 10 cm³ of dimethylformamide each time. 0.55 g of 8-(3,4-dimethyl-1-piperazinyl)-7-fluoro-1-methyl-4-oxo-1,4-dihydro-benzo[b][1,8] naphthyridine-3-carboxylic acid is obtained in the form of a yellow solid melting at 306°–308° C.

EXAMPLE 29

The reaction is carried out under the conditions of Example 28, but starting from 2.3 g of 1-ethyl-7-fluoro-8-(3-methyl-1-piperazinyl)-4-oxo-1,4-dihydrobenzo[b][1,8]naphthyridine-3-carboxylic acid, 2.26 cm³ of 98% formic acid and 5.6 cm³ of a 30% aqueous solution of formaldehyde, 1.75 g of 8-(3,4-dimethyl-1-piperazinyl)-1-ethyl-7-fluoro-4-oxo-1,4-dihydrobenzo[b][1,8]naphthyridine-3-carboxylic acid are obtained in the form of a yellow solid melting at 293°–294° C.

The reaction is carried out under the conditions of Example 28, but from 1.9 g of 1-cyclopropyl-7-fluoro-8-(3-methyl-1-piperazinyl)-4-oxo-1,4-dihydrobenzo[b][1,8]naphthyridine-3-carboxylic acid, 1.38 cm³ of formic acid and 3.30 cm³ of a 30% aqueous solution of formaldehyde. After recrystallizing the crude product from 50 cm³ of ethanol, 1.3 g of 1-cyclopropyl-8-(3,4-dimethyl-1-piperazin-yl)-7-fluoro-4-oxo-1,4-dihydrobenzo[b][1,8]naphthyridine-3-carboxylic acid are obtained in the form of a yellow solid melting at 219° C.

EXAMPLE 31

A suspension of 0.85 g of 1-cyclopropyl-3-ethoxycarbonyl-7-fluoro-8-(4-methyl-1-pip-erazinyl)-4 -oxo-1,4-dihydro-benzo[b][1,8]naphthyridine in 12 cm³ of ethanol, 5 cm³ of 2 N aqueous potassium hydroxide solution and 7 cm³ of water is heated at a temperature close to 80° C. for 1 hour. After adding 5.8 cm³ of a 10% aqueous solution of acetic acid, the precipitate obtained is drained and washed with 3 times 5 cm³ of water. After recrystallizing twice from a mixture of 7.5 cm³ of ethanol and 7.5 cm³ of dimethylformamide each time, 0.4 g of 1-cyclopropyl-7-fluoro-8-(4-methyl-1-piperazinyl)-4-oxo-1,4-dihydrobenzo[b][1,8]naphthyridine-3-carboxylic acid is obtained in the form of a yellow solid melting at 250° C.

The 1-cyclopropyl-3-ethoxycarbonyl-7-fluoro-8-(4-methyl-1-piperazinyl)-4-oxo-1,4-dihydrobenzo[b][1,8-]naphthyridine can be prepared in the following manner:

A suspension of 1.2 g of 1-cyclopropyl-3-ethoxycarbonyl-7,8-difluoro-4-oxo-1,4-dihydrobenzo[b][1,8-]naphthyridine in 1.4 g of 1-methylpiperazine and 20 cm³ of dimethyl sulphoxide is heated at a temperature close to 95° C. for 45 minutes. After cooling to a temperature close to 20° C., the reaction mixture is diluted with 100 cm³ of water and extracted with 3 times 30 cm³ of trichloromethane. The combined organic extracts are washed with 3 times 30 cm³ of water, dried over magnesium sulphate, filtered and concentrated under reduced pressure (20 kPa) at a temperature close to 50° C. The solid obtained is taken up in 20 cm³ of diisopropyl ether, drained, washed with 10 cm³ of the same solvent and recrystallized from 150 cm³ of ethyl acetate. 1.1 g of 1-cyclopropyl-3-ethoxycarbonyl-7-fluoro-8-(4-methyl-1-piperazinyl)-4-oxo-1,4-dihydrobenzo[b][1,8]naphthyridine are obtained in the form of a yellow solid melting at 223° C.

EXAMPLE 32

A suspension of 0.98 g of 3-ethoxycarbonyl-7-fluoro-1-methoxy-8-(4-methyl-1-piperazinyl)-4-oxo-1,4-dihydro-benzo[b][1,8]naphthyridine in 15 cm³ of ethanol, 9 cm³ of water and 6 cm³ of 2 N aqueous potassium hydroxide solution is stirred at a temperature close to 20° C. for 1 hour. 6 cm³ of 2 N methanesulphonic acid are added to the solution obtained and the mixture is extracted with 3 times 10 cm³ of trichloromethane. The combined organic extracts are washed with 3 times 5 cm³ of water, dried over magnesium sulphate, filtered and concentrated to dryness under reduced pressure (20 kPa) at about 50° C. The dry extract obtained is taken up in 5 cm³ of diisopropyl ether, drained and washed with twice 2 cm³ of the same solvent. After recrystallizing once from 30 cm³ of dimethylformamide containing 30% of ethanol, 0.3 g of 7-fluoro-1-methoxy-8-(4-methyl-1-piperazinyl)-4-oxo-1,4-dihydrobenzo[b][1,8]naphthyridine-3-carboxylic acid is obtained in the form of a brown solid melting at 270° C.

The 3-ethoxycarbonyl-7fluoro-1methoxy-8-(4-methyl-1-piperazinyl)-4-oxo-1,4-dihydrobenzo[b][1,8]naphthyridine is prepared under the following conditions:

A suspension of 1.17 g of 3-ethoxycarbonyl-7,8-difluoro-1-methoxy-4-oxo-1,4-dihydrobenzo[b][1,8-]naphthyridine and 0.7 g of 1-methylpiperazine in 15 cm³ of dimethyl sulphoxide is heated at a temperature close to 95° C. for 30 minutes. After cooling to a temperature close to 20° C., the reaction mixture is poured into 60 cm³ of water and the mixture is extracted with 3 times 25 cm³ of trichloromethane. The combined organic extracts are washed with 3 times 25 cm³ of water, dried over magnesium sulphate, filtered and concentrated under reduced pressure (20 kPa) at a temperature close to 50° C. The solid obtained is taken up in 10 cm³ of diisopropyl ether, drained and washed with 5 cm³ of the same solvent. After recrystallizing from 90 cm³ of ethanol, 1.18 g of 3-ethoxycarbonyl-7-fluoro-1-methoxy-8-(4-methyl-1-piperazinyl)-4-oxo-1,4-dihydrobenzo[b][1,8]naphthyridine are obtained in the form of a yellow solid melting at 230° C.

EXAMPLE 33

In carrying out the reaction under the conditions of Example 35 below, but starting from 2 g of 3-ethoxycarbonyl-7,9-difluoro-1-methyl-4-oxo-8-(perhydro-1,4-diazepin-1-yl)-1,4-dihydro-benzo[b][1,8]naphthyridine, 1.5 g of 7,9-difluoro-1-methyl-4-oxo-8 -(perhydro-1,4-diazepin-1-yl)-1,4-dihydro-benzo[b][1,8]naphthyridine-3-carboxylic acid are obtained in the form of a yellow solid melting at 340°-342° C.

The 3-ethoxycarbonyl-7,9-difluoro-1-methyl-4-oxo-8-(perhydro-1,4-diazepin-1-yl)-1,4-dihydrobenzo[b][1,8]naphthyridine was prepared under the conditions of Example 3, but starting from 2 g of 3-ethoxycarbonyl-7,8,9-trifluoro-1-methyl-4-oxo-1,4-dihydro-benzo[b][1,8]naphthyridine and 2 g of hexahydro-1,4-diazepine. 2 g of 3-ethoxycarbonyl-7,9-difluoro-1-methyl-4-oxo-8-(perhydro-1,4-diazepin-1-yl)-1,4-dihydro-benzo[b][1,8]naphthyridine are obtained in the form of a yellow solid melting at 226° C.

EXAMPLE 34

A suspension of 0.8 g of 3-ethoxycarbonyl-7,9-difluoro-1-methyl-4-oxo-8-(1-piperazinyl)-1,4-dihydrobenzo[b][1,8]naphthyridine in 20 cm³ of ethanol and 20 cm³ of N aqueous potassium hydroxide solution is heated at a temperature close to 75° C. for 1 hour and a half. 12 g of a 10% aqueous acetic acid solution are added to the solution obtained, at this temperature. The insoluble matter obtained is drained at about 75° C. and washed 3 times with 30 cm³ of water at about 20° C. After recrystallizing once from 90 cm³ of dimethylformamide, 0.5 g of 7,9-difluoro-1-methyl-4-oxo-8-(1-piperazinyl)-1,4-dihydro-benzo[b][1,8]naphthyridine-3-carboxylic acid is obtained in the form of a yellow solid melting at 345°-347° C.

The 3-ethoxycarbonyl-7,9-difluoro-1-methyl-4-oxo-8-(1-piperazinyl)-1,4-dihydro-benzo[b][1,8]-naphthyridine was prepared in the following manner:

A suspension of 2 g of 3-ethoxycarbonyl-7,8,9-trifluoro-1-methyl-4-oxo-1,4-dihydrobenzo[b][1,8]naphthyridine in 30 cm³ of dimethyl sulphoxide and 5 g of piperazine is heated at a temperature close to 100° C., with stirring, for 2 hours. The solution obtained at about 100° C. is poured, with stirring, into a mixture of 150 cm³ of water and 50 g of ice. The solution is extracted with 3 times 40 cm³ of trichloromethane. The combined organic phases are extracted with twice 50 cm³ of 0.1 N methanesulphonic acid. 10 g of potassium carbonate are added to the combined aqueous phases. The mixture is extracted with 3 times 40 cm³ of trichloromethane. The combined organic extracts are washed with twice 50 cm³ of water, dried over magnesium sulphate, filtered and concentrated to dryness under reduced pressure (20 kPa) at about 50° C. The residue obtained is recrystallized from 25 cm³ of ethanol. 0.8 g of 3-ethoxycarbonyl-7,9-difluoro-1-methyl-4-oxo-8-(1-piperazinyl)-1,4-dihydrobenzo[b][1,8]naphthyridine is obtained in the form of a yellow solid melting at 221° C.

EXAMPLE 35

A suspension of 1.5 g of (RS)-3-ethoxycarbonyl-7,9-difluoro-1-methyl-8-(3-methyl-1-piperazinyl)-4-oxo-1,4-dihydro-benzo[b][1,8]naphthyridine in 20 cm³ of ethanol and 20 cm³ of N aqueous potassium hydroxide solution is heated at a temperature close to 75° C. for 1 hour and a half. 12 g of a 10% aqueous solution of acetic acid is added to the solution obtained, at this latter temperature. The insoluble matter obtained is drained at about 75° C. and washed 3 times with 30 cm³ of water at about 20° C. After recrystallizing once from 100 cm³ of dimethylformamdide, 0.9 g of (RS)-7,9-difluoro-1-methyl-8-(3-methyl-1-piperazinyl)-4-oxo-1,4-dihydro-benzo[b][1,8]naphthyridine-3-carboxylic acid is obtained in the form of a yellow solid melting at 380°–382° C.

The (RS)-3-ethoxycarbonyl-7,9-difluoro-1-methyl-8-(3-methyl-1-piperazinyl)-4-oxo-1,4-dihydrobenzo[b][1,8]naphthyridine was prepared in the following manner:

A suspension of 2 g of 3-ethoxycarbonyl-7,8,9-trifluoro-1-methyl-4-oxo-1,4-dihydrobenzo[b][1,8]naphthyridine in 30 cm³ of dimethyl sulphoxide and 5 g of 2-methylpiperazine is heated at a temperature close to 100° C., with stirring, for 2 hours. The solution obtained is poured, at this temperature, with stirring, into a mixture of 150 cm³ of water and 50 g of ice. 5 g of potassium carbonate are added at about 20° C. and the mixture is extracted with 3 times 50 cm³ of trichloromethane. The combined organic extracts are washed with twice 50 cm³ of water, dried over magnesium sulphate, filtered and concentrated to dryness under reduced pressure (20 kPa) at about 50° C. The residue obtained is recrystallized from 30 cm³ of ethanol. 1.6 g of (RS)-3-ethoxycarbonyl-7,9-difluoro-1-methyl-8-(3-methyl-1-piperazinyl)-4-oxo-1,4-dihydrobenzo[b][1,8]naphthyridine are obtained in the form of a yellow solid melting at 240° C.

EXAMPLE 36

Carrying out the reaction under the conditions of Example 35, but starting from 1 g of 3-ethoxycarbonyl-1-ethyl-7,9-difluoro-4-oxo-8-(1-piperazinyl)-1,4-dihydro-benzo[b][1,8]naphthyridine, 0.7 g of 1-ethyl-7,9-difluoro-4-oxo-8-(1-piperazinyl)-1,4-dihydrobenzo[b][1,8]naphthyridine-3-carboxylic acid is obtained in the form of a yellow solid melting at 340°–342° C.

The 3-ethoxycarbonyl-1-ethyl-7,9-difluoro-4-oxo-8-(1-piperazinyl)-1,4-dihydro-benzo[b][1,8]naphthyridine was prepared under the conditions of Example 35, but starting from 1.75 g of 3-ethoxycarbonyl-1-ethyl-7,8,9-trifluoro-4-oxo-1,4-dihydro-benzo[b][1,8]naphthyridine and 4.3 g of piperazine, 1.1 g of 3-ethoxycarbonyl-1-ethyl-7,9-difluoro-4-oxo-8-(1-piperazinyl)-1,4-dihydrobenzo[b][1,8]naphthyridine are obtained in the form of a yellow solid melting at 229° C.

EXAMPLE 37

Carrying out the reaction under the conditions of Example 35, but starting from 1.1 g of 3-ethoxycarbonyl-1-ethyl-7,9-difluoro-8-(4-methyl-1-piperazinyl)-4-oxo-1,4-dihydrobenzo[b][1,8]naphthyridine, 0.75 g of 7,9-difluoro-1-ethyl-8-(4-methyl-1-piperazinyl)-4-oxo-1,4-dihydrobenzo[b][1,8]naphthyridine-3-carboxylic acid is obtained in the form of a yellow solid melting at 308° C.

The 3-ethoxycarbonyl-1-ethyl-7,9-difluoro-8-(4-methyl-1-piperazinyl)-4-oxo-1,4-dihydrobenzo[b][1,8]naphthyridine was prepared under the conditions of Example 3 but starting from 1.4 g of 3-ethoxycarbonyl-1-ethyl-7,8,9-trifluoro-4-oxo-1,4-dihydro-benzo[b][1,8]naphthyridine and 4 g of 1-methylpiperazine. 1.1 g of 3-ethoxycarbonyl-1-ethyl-7,9-difluoro-8-(4-methyl-1-piperazinyl)-4-oxo-1,4-dihydro-benzo[b][1,8]naphthyridine are obtained in the form of a yellow solid melting at 206° C.

The 3-ethoxycarbonyl-1-ethyl-7,8,9-trifluoro-4-oxo-1,4-dihydro-benzol[b][1,8]naphthyridine was prepared under the following conditions:

4.5 g of ethylamine are added in the course of 10 minutes, at between 5° and 10° C., to a stirred suspension of 7.1 g of ethyl 2-(2-chloro-6,7,8-trifluoroquinoline-3-carbonyl)-3-dimethylaminoacrylate in 100 cm³ of ethanol kept at a temperature close to 5° C., the mixture is stirred for 1 hour at between 5° and 10° C. and the temperature is allowed to rise to about 20° C. 4 g of 1,8-diazobicyclo[5.4.0]undec-7-ene (DBU) are added to the solution obtained and the mixture is heated at a temperature close to 75° C. for 1 hour and a half. After cooling to a temperature close to 20° C., the product is drained and washed with twice 30 cm³ of ethanol and twice 50 cm³ of diisopropyl ether. 4 g of 3-ethoxycarbonyl-1-ethyl-7,8,9-trifluoro-4-oxo-1,4-dihydro-benzo[b][1,8]naphthyridine are obtained in the form of a cream solid melting at 284° C., which is used for the subsequent steps without further purification.

EXAMPLE 38

Carrying out the reaction under the conditions of Example 35, but starting from 1.7 g of 7,9-difluoro-3-ethoxycarbonyl-1-ethyl-4-oxo-8-(perhydro-1,4-diazepin-1-yl)-1,4-dihydro-benzo[b][1,8]naphthyridine, 1.1 g of 1-ethyl-7,9-difluoro-4-oxo-8-(perhydro-1,4-diazepin-1-yl)-1,4-dihydro-benzo[b][1,8]naphthyridine-3-carboxylic acid are obtained in the form of a yellow solid melting at 274° C.

The 7,9-difluoro-3-ethoxycarbonyl-1-ethyl-4-oxo-8-(perhydro-1,4-diazepin-1-yl)-1,4-dihydrobenzo[b][1,8-]naphthyridine was prepared under the conditions of Example 5, but starting from 3 g of 3-ethoxycarbonyl-1-ethyl-7,8,9-trifluoro-4-oxo-1,4-dihydro-benzo[b][1,8-]naphthyridine and 2 g of hexahydro-1,4-diazepine. 1.7 g of 3-ethoxycarbonyl-1-ethyl-7,9-difluoro-4-oxo-8-(perhydro-1,4-diazepin-1-yl)-1,4-dihydro-benzo[b][1,8-]naphthyridine are obtained in the form of a yellow solid melting at 190° C.

EXAMPLE 39

The reaction is carried out under the conditions of Example 35, but starting from 2 g of 3-ethoxycarbonyl-7,9-difluoro-4-oxo-8-(1-piperazinyl)-1-tert.-butyl-1,4-dihydro-benzo[b][1,8]naphthyridine. After recrystallizing from 35 cm³ of dimethylformamide and 35 cm³ of ethanol, 1 g of 7,9-difluoro-4-oxo-8-(1-piperazinyl)-1-tert.-butyl-1,4-dihydro-benzo[b][1,8]naphthyridine-3-carboxylic acid is obtained in the form of a yellow solid melting at 318° C.

The 3-ethoxycarbonyl-7,9-difluoro-4-oxo-8-(1-piperazinyl)-1-tert.-butyl-1,4-dihydro-benzo[b][1,8-]naphthyridine was prepared under the conditions of Example 35, but starting from 1.9 g of 3-ethoxycarbonyl-7,8,9-trifluoro-4-oxo-1-tert.-butyl-1,4-dihydro-benzo[b][1,8]naphthyridine and 4.3 g of piperazine. After recrystallizing once from 50 cm³ of diisopropyl ether and 10 cm³ of propan-2-ol, 2 g of 3-ethoxycarbonyl-7,9-difluoro-4-oxo-8-(1-piperazinyl)-1-tert.-butyl-1,4-dihydro-benzo[b][1,8]naphthyridine are obtained in the form of a yellow solid melting at 186° C.

The 3-ethoxy-carbonyl-7,8,9-trifluoro-4-oxo-1-tert.-butyl-1,4-dihydro-benzo[b][1,8]naphthyridine was prepared under the following conditions:

9.5 g of tert.-butylamine are added at a temperature of about 20° C., in the course of 5 minutes, to a stirred solution of 11.7 g of ethyl 2-(2-chloro- 6,7,8-trifluoroquinoline-3-carbonyl)-3-dimethylaminoacrylate in 150 cm³ of trichloromethane at the same temperature. After stirring for 4 hours at about 20° C., the solution is concentrated to dryness under reduced pressure (20 kPa) at about 50° C. The residue obtained is taken up in 100 cm³ of ethanol. 5 g of DBU are added to the solution obtained and the mixture is heated at a temperature close to 75° C. for 3 hours. After cooling to about 20° C., the precipitate obtained is drained and washed with twice 50 cm³ of ethanol and twice 50 cm³ of diisopropyl ether. 9.5 g of 3-ethoxycarbonyl-7,8,9-trifluoro-4-oxo-1-tert.-butyl-1,4-dihydro-benzo[b][1,8]naphthyridine are obtained in the form of a colourless solid melting at 229° C., which is used for the subsequent steps without further purification.

EXAMPLE 40

Carrying out the reaction under the conditions of Example 35, but starting from 1 g of 1-cyclopropyl-3-ethoxycarbonyl-7,9-difluoro-4-oxo-8-(1-piperazinyl)-1,4-dihydro-benzo[b][1,8]naphthyridine, 0.70 g of 1-cyclopropyl-7,9-difluoro-4-oxo-8-(1-piperazinyl)-1,4-dihydro-benzo[b][1,8]naphthyridine-3-carboxylic acid is obtained in the form of a yellow solid melting at 305°–307° C.

The 1-cyclopropyl-3-ethoxycarbonyl-7,9-difluoro-4-oxo-8-(1-piperazinyl)-1,4-dihydro-benzo[b][1,8]naphthyridine was prepared under the conditions of Example 35 but starting from 1.5 g of 1-cyclopropyl-3-ethoxycarbonyl-7,8,9-trifluoro-4-oxo-1,4-dihydrobenzo[b][1,8]naphthyridine and 2.7 g of piperazine. After recrystallizing once from 40 cm³ of propan-2-ol, 1 g of 1-cyclopropyl-3-ethoxycarbonyl-7,9-difluoro-4-oxo-8-(1-piperazinyl)-1,4-dihydro-benzo[b][1,8]naphthyridine is obtained in the form of a yellow solid melting at 256° C.

EXAMPLE 41

The reaction is carried out under the conditions of Example 35, but starting from 1.7 g of 1-cyclopropyl-3-ethoxycarbonyl-7,9-difluoro-8-(4-methyl-1-piperazinyl)-4-oxo-1,4-dihyhdro-benzo[b][1,8]naphthyridine. After recrystallizing from 60 cm³ of ethanol, 1.3 g of 1-cyclopropyl-7,9-difluoro-8-(4-methyl-1-piperazin-yl)-4-oxo-1,4-dihydrobenzo[b][1,8]naphthyridine-3-carboxylic acid are obtained in the form of an orange solid melting at 248° C.

The 1-cyclopropyl-3-ethoxycarbonyl-7,9-difluoro-8-(4-methyl-!-piperazinyl)-4-oxo-1,4-dihydrobenzo[b][1,8-]naphthyridine was prepared under the conditions of Example 35 but starting from 1.5 g of 1-cyclopropyl-3-ethoxycarbonyl-7,8,9-trifluoro-4-oxo-1,4-dihydro-benzo[b][1,8]naphthyridine and 3 g of 1-methylpiperazine. methylpiperazine. 1.5 g of 1-cyclopropyl-3-ethoxycarbonyl-7,9-difluoro-8-(4-methyl-1-piperazinyl)-4-oxo-1,4-dihydro-benzo[b][1,8]naphthyridine are obtained in the form of a yellow solid melting at 230° C.

EXAMPLE 42

The reaction is carried out under the conditions of Example 35, but starting from 1.9 g of (RS)-1-cyclopropyl-3-ethoxycarbonyl-7,9-difluoro-8-(3-methyl-1-piperazinyl)-4-oxo-1,4-dihydro-benzo[b][1,8]naphthyridine. After recrystallizing from a mixture of 20 cm³ of dimethylformamide and 20 cm³ of ethanol, 1.1 g of (RS)-1-cyclopropyl-7,9-difluoro-8-(3-methyl-1-piperazinyl)-4-oxo-1,4-dihydro-benzo[b][1,8]naphthyridine-3-carboxylic acid are obtained in the form of a yellow solid melting at 309° C.

The (RS)-1-cyclopropyl-3-ethoxycarbonyl-7,9-difluoro-8-(3-methyl-1-piperazinyl)-4-oxo-1,4-dihydrobenzo[b][1,8]naphthyridine was prepared under the conditions of Example 35 but starting from 1.8 g of 1-cyclopropyl-3-ethoxycarbonyl-7,8,9-trifluoro-4-oxo-1,4-dihydro-benzo[b][1,8]naphthyridine and 2 g of (RS)-2-methylpiperazine. After recrystallizing once from 15 cm³ of propan-2-ol and 15 cm³ of diisopropyl ether, 1.9 g of (RS)-1-cyclopropyl-3-ethoxycarbonyl-7,9-difluoro-8-(3-methyl-1-piperazinyl)-4-oxo-1,4-dihydrobenzo[b][1,8]naphthyridine are obtained in the form of a yellow solid melting at 190° C.

The present invention also relates to pharmaceutical compositions which can be used in human and veterinary medicine and which contain, as active product, at least one product of general formula (I) in the pure form (in the free form or in the form of a salt) or in the form of a combination with one or more compatible and pharmaceutically acceptable diluents or adjuvants. These compositions can be administered orally, parenterally or rectally.

Solid compositions for oral administration which can be used are tablets, pills, powders or granules. In these compositions the active product according to the invention is mixed with one or more inert diluents or adjuvants, such as sucrose, lactose or starch. These compositions can also contain substances other than the diluents, for example a lubricant such as magnesium stearate.

Liquid compositions for oral administration which can be used are pharmaceutically acceptable emulsions, solutions, suspensions, syrups and elixirs containing inert diluents such as water or paraffin oil. These compositions can also contain substances other than the diluents, for example wetting, sweetening or flavouring products.

The compositions for parenteral administration can be aqueous or non-aqueous sterile solutions, suspensions or emulsions. Substances which can be used as the solvent or vehicle are propylene glycol, a polyethylene glycol, vegetable oils, in particular olive oil, and injectable organic esters, for example ethyl oleate. These compositions can also contain adjuvants, in particular wetting agents, emulsifiers or dispersants. The sterilization can be carried out in several ways, for example with the aid of a bacteriological filter, by incorporating sterilizing agents into the composition, by irradiation or by heating. They can also be prepared in the form of sterile solid compositions, which will be dissolved in sterile water or any other injectable sterile medium at the time of use.

The compositions for rectal administration are suppositories or rectal capsules, which can contain, in addition to the active product, excipients such as cacao butter or suppo-wax.

In human or veterinary therapeutics, the compositions according to the invention are particularly useful for the treatment of infections of bacterial origin.

In general, the physician will determine the dosage which he considers to be most appropriate as a function of the age, the weight, the degree of infection and other factors relating to the subject to be treated. In general, the doses are between 0.2 and 1 g of active product twice per day, by oral or parenteral route for an adult.

The following example, given as a non-limiting example, illustrates a composition according to the invention:

EXAMPLE

Tablets containing a dose of 250 mg of active product and having the following composition are prepared by the customary techniques.

| | |
|---|---|
| 1-cyclopropyl-7-fluoro-8-(1-piperazinyl)-4-oxo-1,4-dihydro-benzo[b] [1,8]-naphthyridine-3-carboxylic acid | 250 mg |
| starch | 50 mg |
| lactose | 35 mg |
| talc | 15 mg |

The products of general formula (I) are also of value in the field of agrochemistry for the antibacterial treatment of plants and vegetables. It is understood that the compositions for agrochemical use containing a product of general formula (I) also fall within the scope of the present invention.

Moreover, the products of general formula (I) can also be used as preservatives or disinfectants for organic or inorganic materials. In particular in the dyestuffs, fatty matter, paper, wood and polymer industries or in the textile industry, the foodstuffs industry or water treatment. It is also understood that the compositions containing a product of general formula (I) in the pure form or in the form of a combination with compatible diluents or adjuvants, also fall within the scope of the present invention.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. A benzo(b)(1,8)naphthyridine compound, comprising the formula:

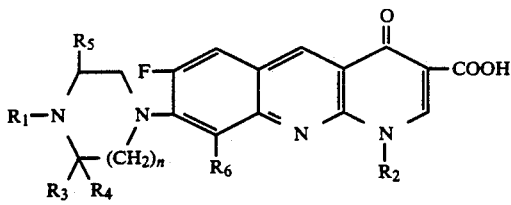

wherein,
$R_1$ represents a hydrogen atom or an alkyl or hydroxyalkyl radical,
$R_2$ represents a hydrogen atom or an alkyl, fluoroalkyl, cycloalkyl, alkoxy or alkylamino radical,
$R_3$ represents an alkyl radical, and
$R_4$ and $R_5$ are different and represent a hydrogen atom or an alkyl radical, or
$R_3$ represents a hydrogenation or an alkyl or cycloalkyl radical and
$R_4$ and $R_5$ are hydrogen atoms,
$R_6$ represents a hydrogen or fluorine atom and n is equal to 1 or 2,
the alkyl radicals containing 1 to 4 carbon atoms in a straight or branched chain and the cycloalkyl radicals containing 3 to 6 carbon atoms, or a pharmaceutically acceptable metal salt thereof, its addition salts with nitrogenous bases or its acid addition salts as well as its hydrated forms and, where appropriate, its isomers and their mixtures.

2. A benzonaphthyridine compound according to claim 1, wherein
$R_1$ represents a hydrogen atom or an alkyl radical containing 1 or 2 carbon atoms which is optionally substituted by a hydroxyl radical,
$R_2$ represents a hydrogen atom or a straight-chain or branched alkyl radical containing 1 to 4 carbon atoms, which is optionally substituted by a fluorine atoms,
$R_3$ represents a methyl radical and
$R_4$ and $R_5$, which are different, represent a hydrogen atom or a methyl radical, or
$R_3$ is a hydrogen atom or a methyl radical and $R_4$ and $R_5$ represent hydrogen atoms,
$R_6$ represents a hydrogen or fluorine atom and
n is equal to 1 or 2, or a pharmaceutically acceptable metal salt thereof, its addition salts with nitrogenous bases or its acid addition salts as well as its hydrated forms and, where appropriate, its isomers and their mixtures.

3. 7-Fluoro-1-methyl-8-(3-methyl-1-piperazinyl)-4-oxo-1,4-dihydro-benzo[b][1,8]naphthyridine-3-carboxylic acid and or a pharmaceutically acceptable metal salt thereof.

4. 1-Ethyl-7-fluoro-8-(1-piperazinyl)-4-oxo-1,4-dihydro-benzo[b][1,8]naphthyridine-3-carboxylic acid and or a pharmaceutically acceptable metal salt thereof.

5. 1-Cyclopropyl-7-fluoro-8-(1-piperazinyl)4-oxo-1,4-dihydro-benzo[b][1,8]naphthyridine-3-carboxylic acid and or a pharmaceutically acceptable metal salt thereof.

6. 7,9-Difluoro-1-methyl-8-(4-methyl-1-piperazinyl)-4-oxo-1,4-dihydro-benzo[b][1,8]naphthyridine-3-carboxylic acid and or a pharmaceutically acceptable metal salt thereof.

7. 8-(3,4-Dimethyl-1-piperazinyl)-1-ethyl-7-fluoro-4-oxo-1,4-dihydro-benzo[b][1,8]naphthyridine-3-carboxylic acid and or a pharmaceutically acceptable metal salt thereof.

8. A pharmaceutical composition comprising an effective amount of at least one compound according to claim 1, in the pure form or in combination with one or more compatible diluents or adjuvants.

* * * * *